United States Patent [19]

Sorenson et al.

[11] Patent Number: 4,489,729
[45] Date of Patent: Dec. 25, 1984

[54] ULTRASOUND IMAGING SYSTEM

[75] Inventors: Paul D. Sorenson, Blaine; Larry A. McNichols, Coon Rapids, both of Minn.

[73] Assignee: Medtronic, Inc., Minneapolis, Minn.

[21] Appl. No.: 415,043

[22] Filed: Sep. 3, 1982

[51] Int. Cl.$^3$ .............................................. A61B 10/00
[52] U.S. Cl. ...................................... 128/660; 73/626
[58] Field of Search .................. 128/660, 661, 6 63; 73/620–621, 625–626

[56] References Cited

U.S. PATENT DOCUMENTS

| | | | |
|---|---|---|---|
| 3,681,977 | 8/1972 | Wendt et al. | 128/660 |
| 3,888,238 | 6/1975 | Meindl et al. | 128/660 |
| 4,215,584 | 8/1980 | Kurada et al. | 128/660 X |
| 4,242,912 | 1/1981 | Burckhardt et al. | 73/626 |
| 4,245,250 | 1/1981 | Tiemann | 358/140 |
| 4,246,791 | 1/1981 | Glenn | 73/620 |
| 4,252,026 | 2/1981 | Robinson | 73/626 |
| 4,253,338 | 3/1981 | Iinuma et al. | 73/626 |
| 4,265,121 | 5/1981 | Cribbs | 73/607 |
| 4,271,706 | 6/1981 | Ledley | 73/614 |
| 4,271,842 | 6/1981 | Specht et al. | 128/661 |
| 4,272,991 | 6/1981 | Cribbs | 73/621 |

*Primary Examiner*—Kyle L. Howell
*Assistant Examiner*—Francis J. Jaworski
*Attorney, Agent, or Firm*—Robert J. Klepinski; Joseph F. Breimayer; John L. Rooney

[57] ABSTRACT

An ultrasound imaging system particularly adapted for detecting structure which reflects ultrasound at a variety of angles. There is a plurality of ultrasound transducers, which may be a linear array or a two-dimension array with the various horizontal rows of the array offset from one another, but having zero horizontal space or overlapping between adjacent vertical transducers. A sequencer causes one transducer to fire and then listen for an echo; if no echo is heard, the same transducer fires again and an adjacent transducer listens; if there is still no echo, the transducer fires and the next adjacent transducer listens; and so on until a predetermined listening sequence is concluded. If an echo is heard at any time, the listening sequence is terminated and the next transducer fires, as determined by a predetermined firing sequence, and the listening sequence for that firing transducer is conducted until an echo is heard or the listening sequence is completed; and so on until the firing sequence is completed. A counter measures the time between the transducer firing and the receipt of the echo to produce a range signal representative of the distance from the transducer face to the structure producing the echo. The signals produced by the transducers upon receipt of the echo and the range signal are processed by computer to produce a visual representation of the structure imaged, such as spine and rib structure.

8 Claims, 30 Drawing Figures

Microfiche Appendix Included
(1 microfiche, 56 pages)

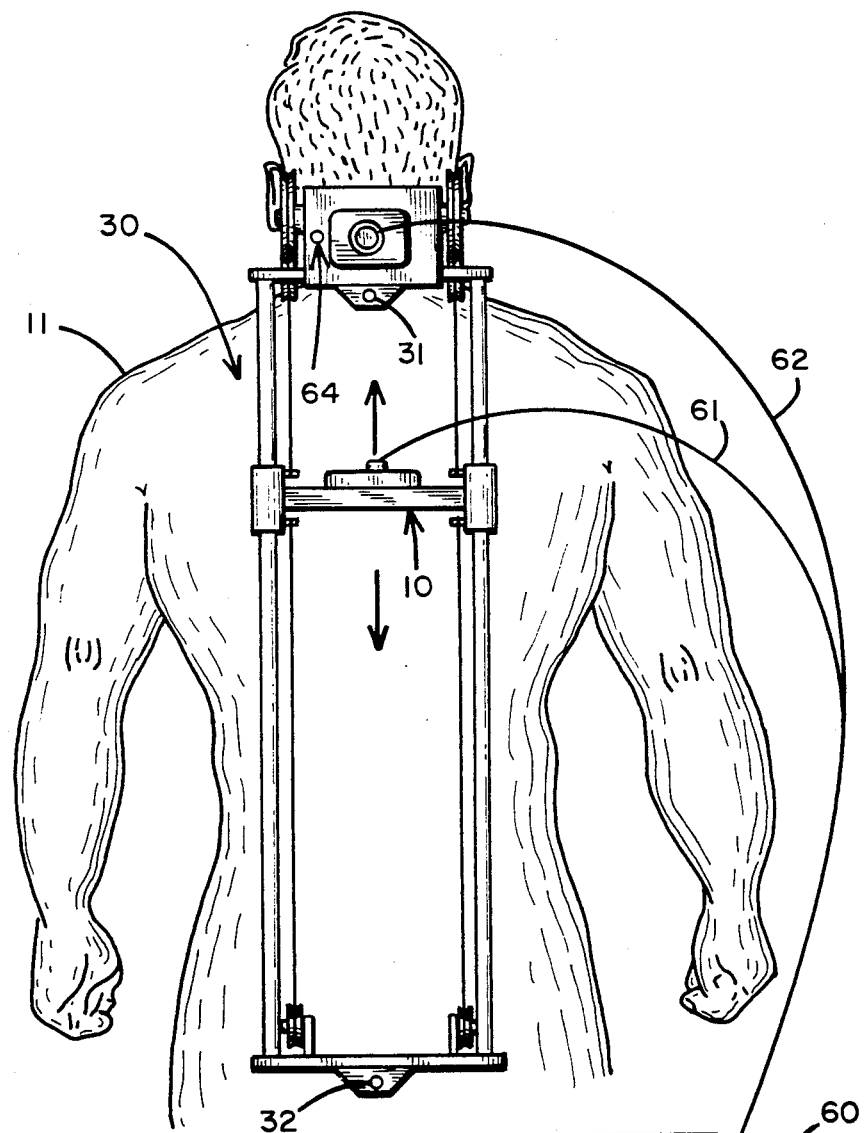
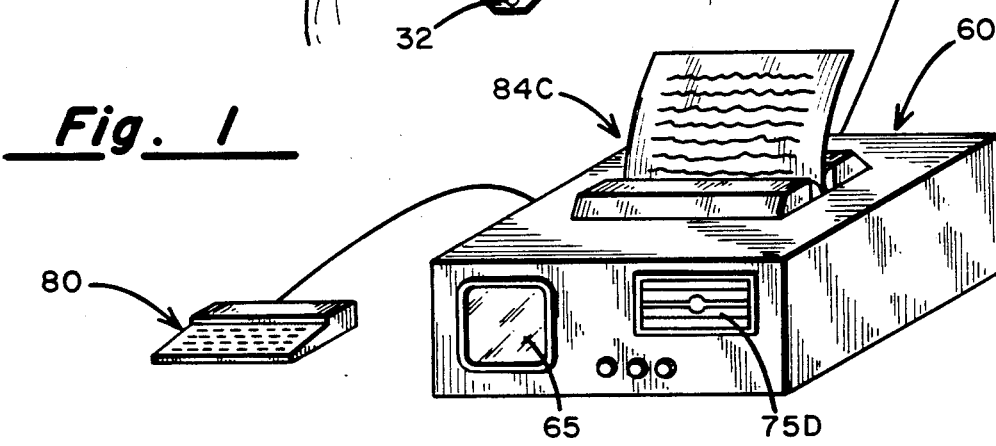
Fig. 1

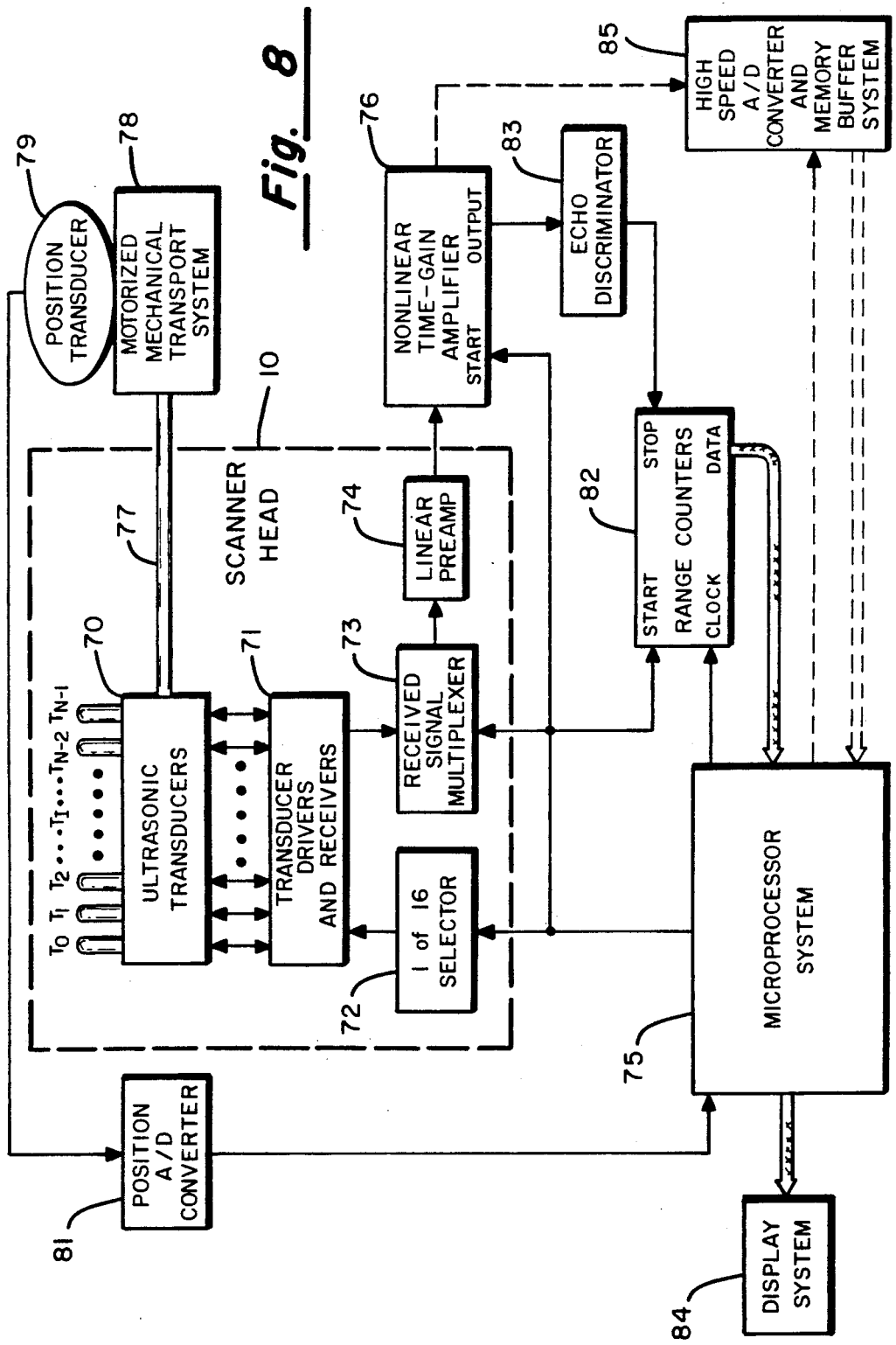

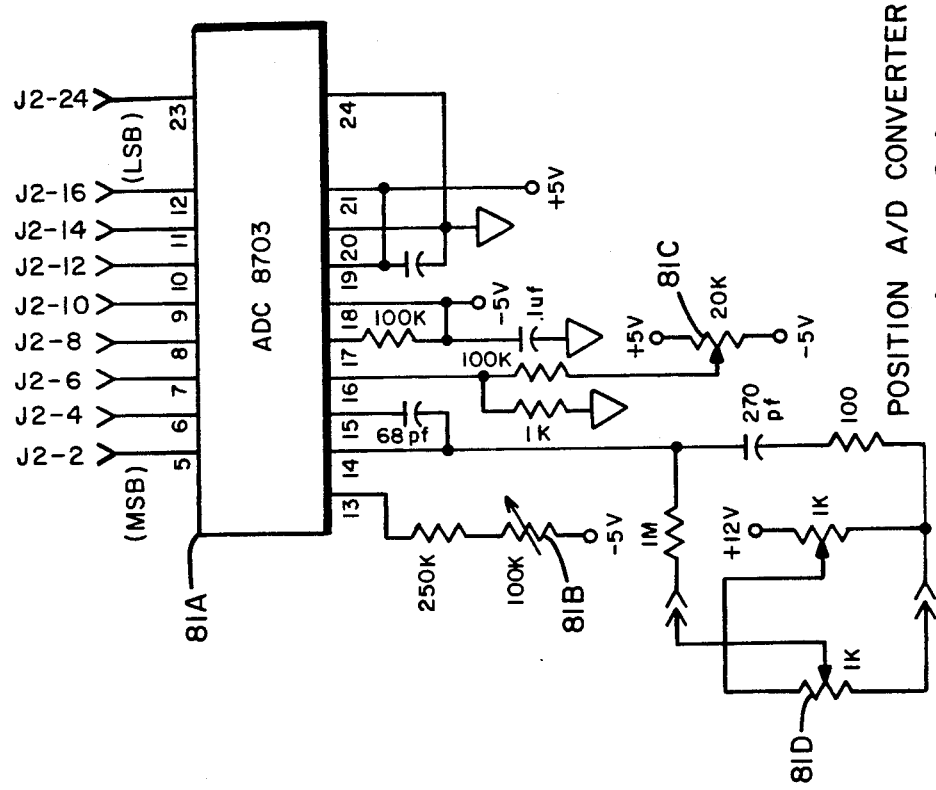
Fig. 9b POSITION A/D CONVERTER
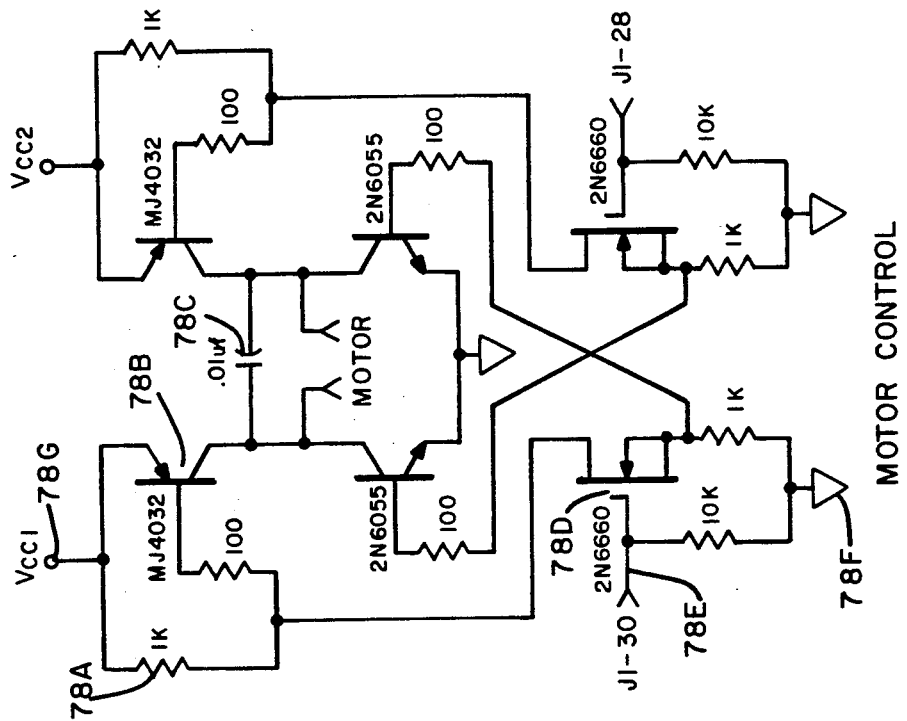
Fig. 9a MOTOR CONTROL

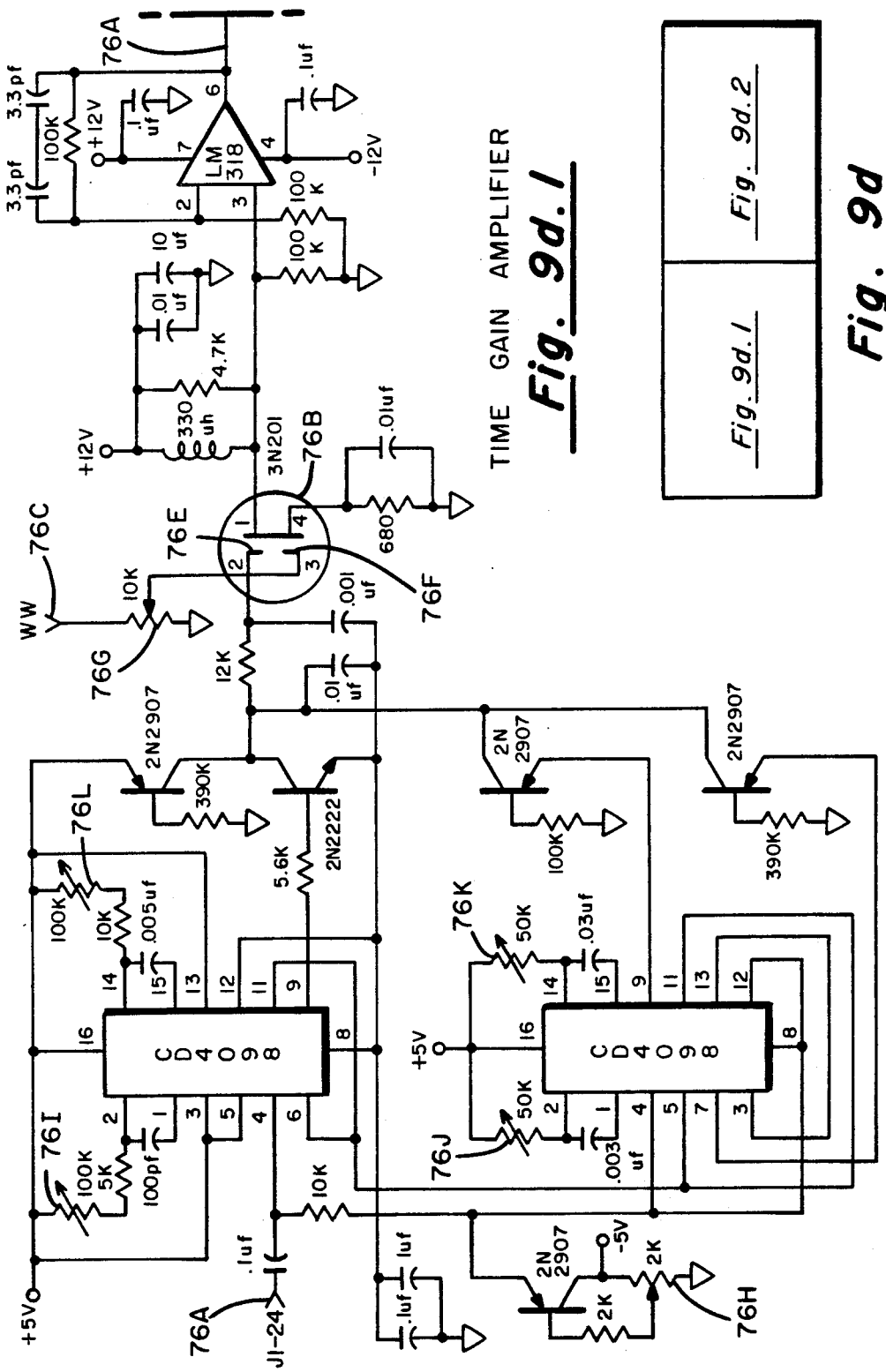
Fig. 9d.1
TIME GAIN AMPLIFIER

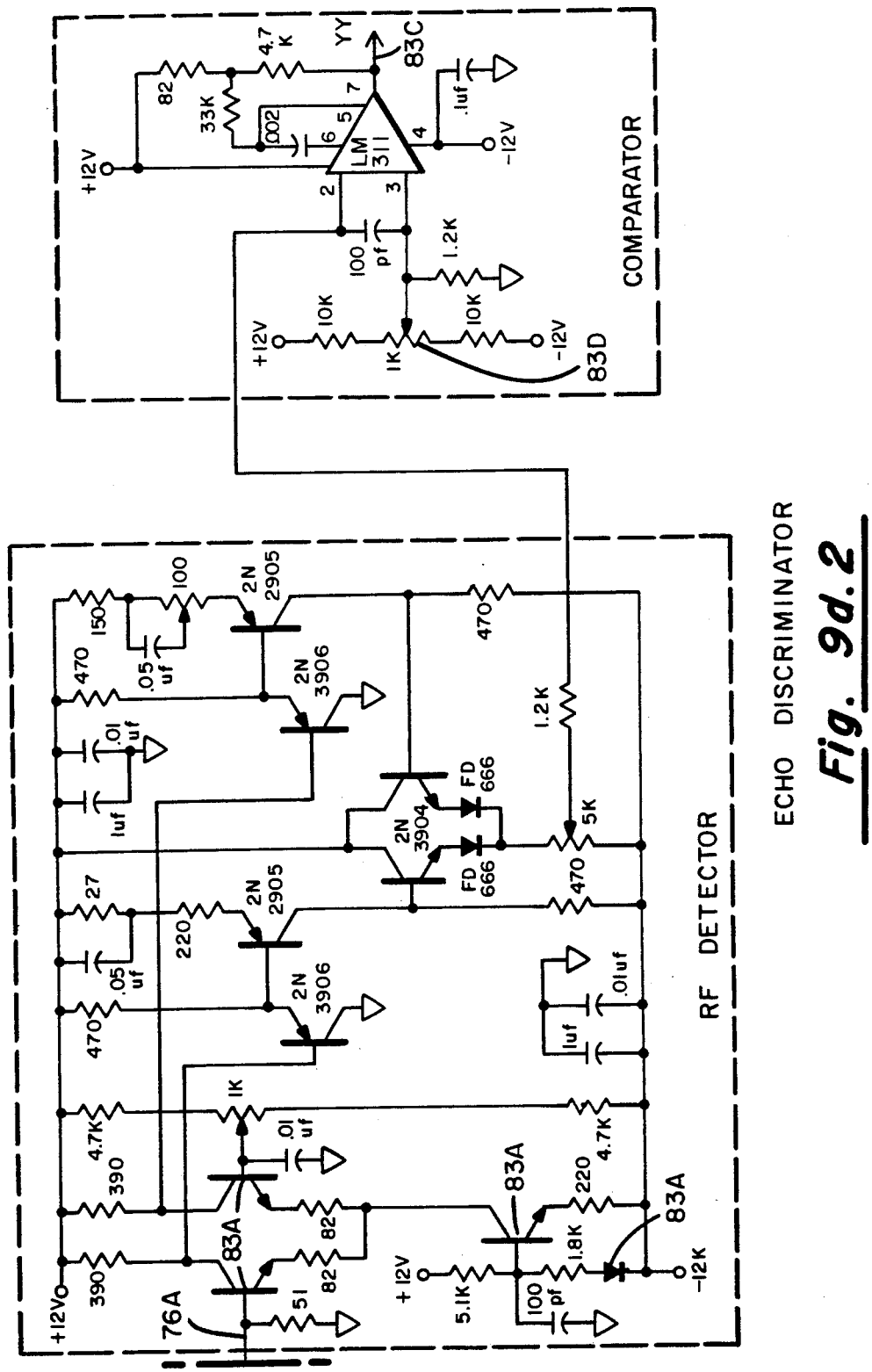
Fig. 9d.2

RANGE COUNTER #1

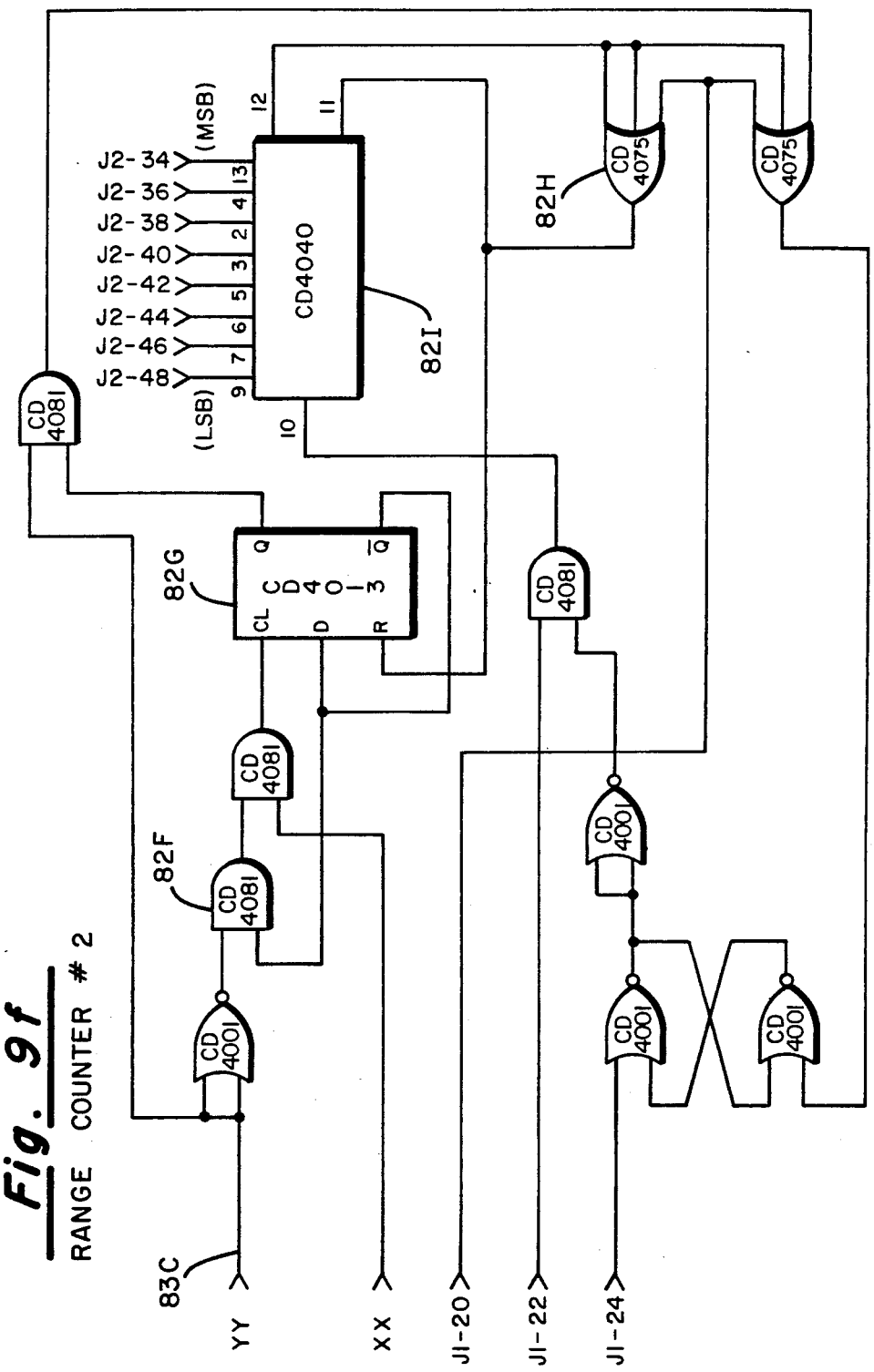
Fig. 9f  RANGE COUNTER #2

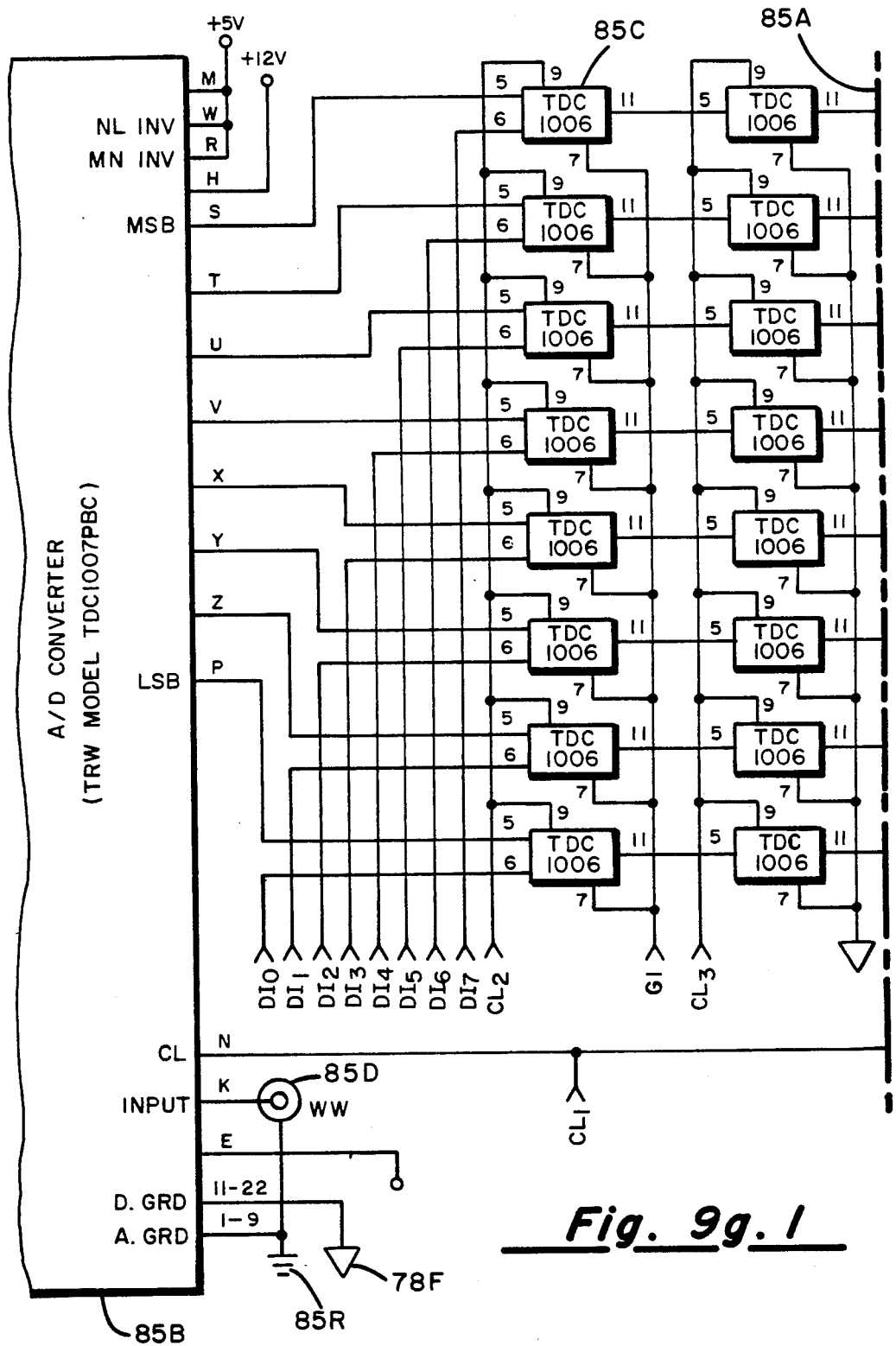
*Fig. 9g.1*

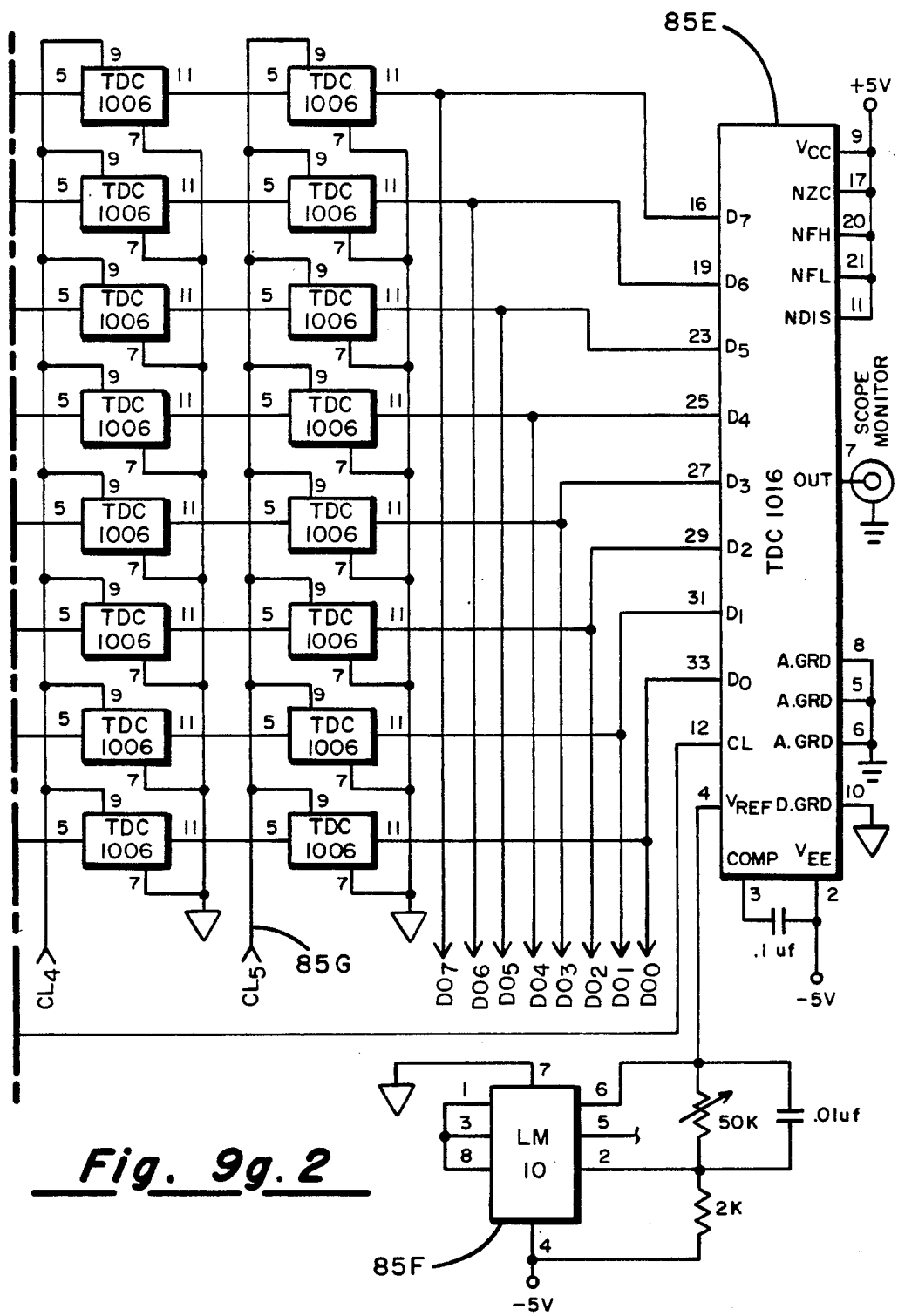
Fig. 9g.2

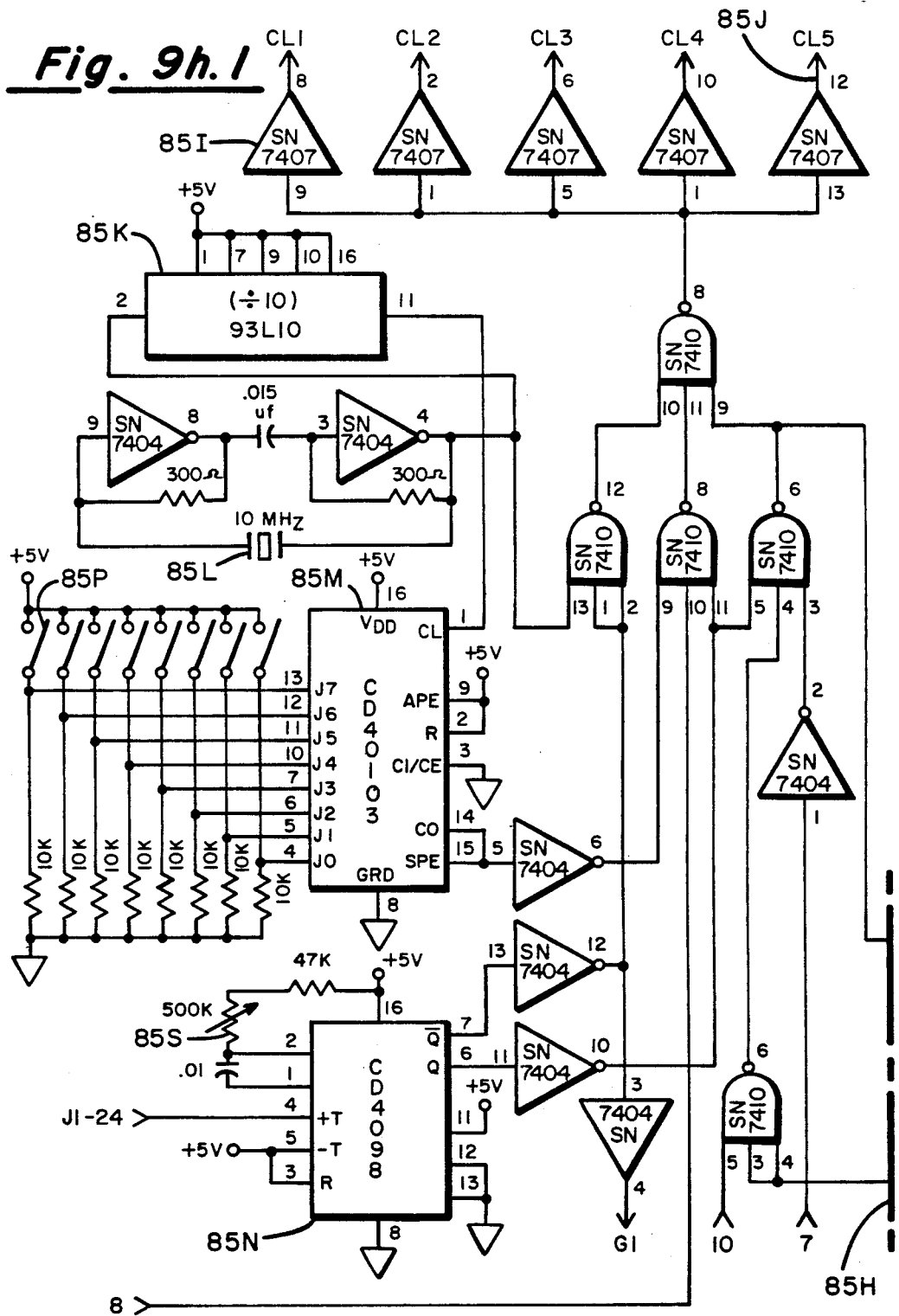
Fig. 9h.1

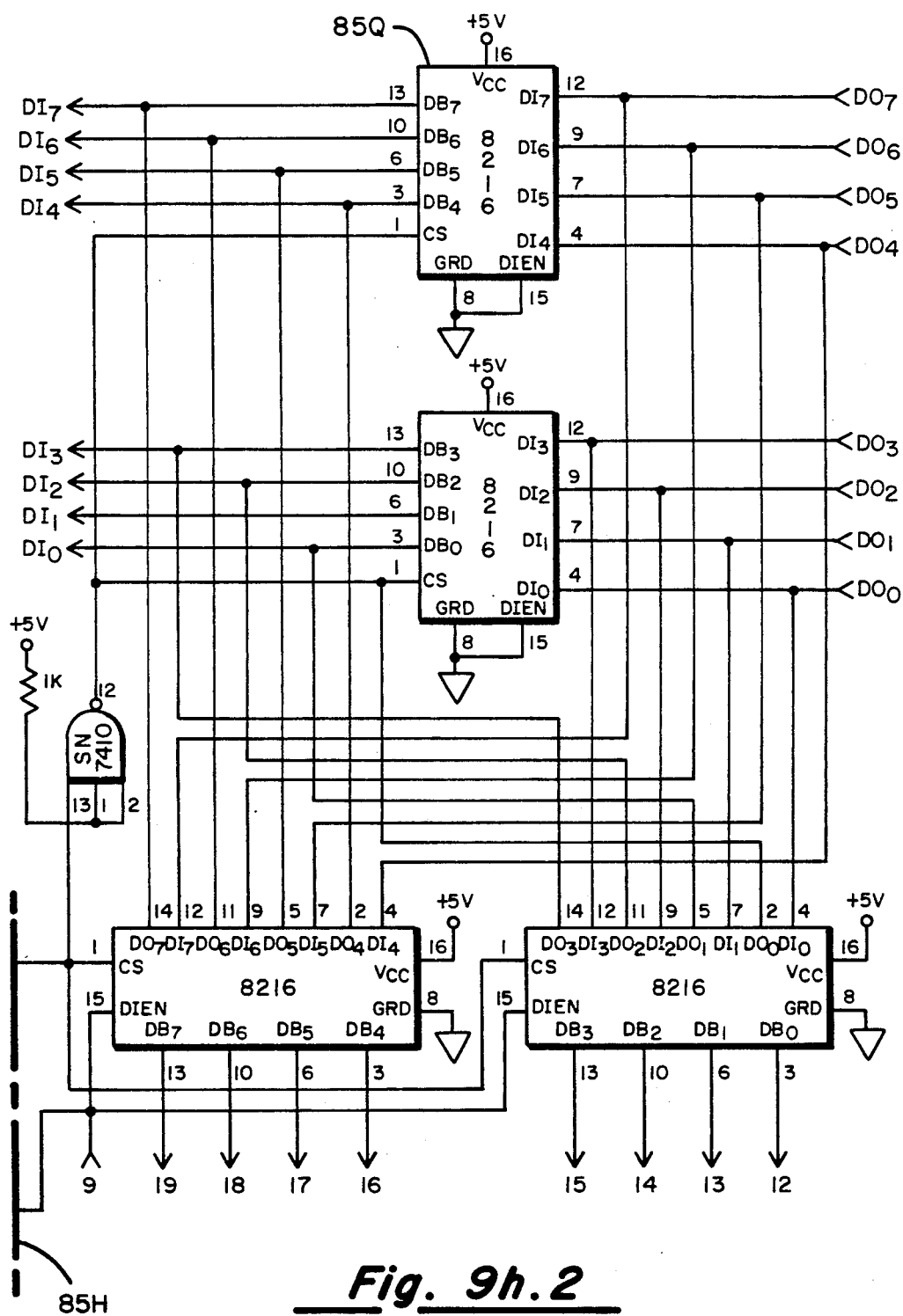
Fig. 9h.2

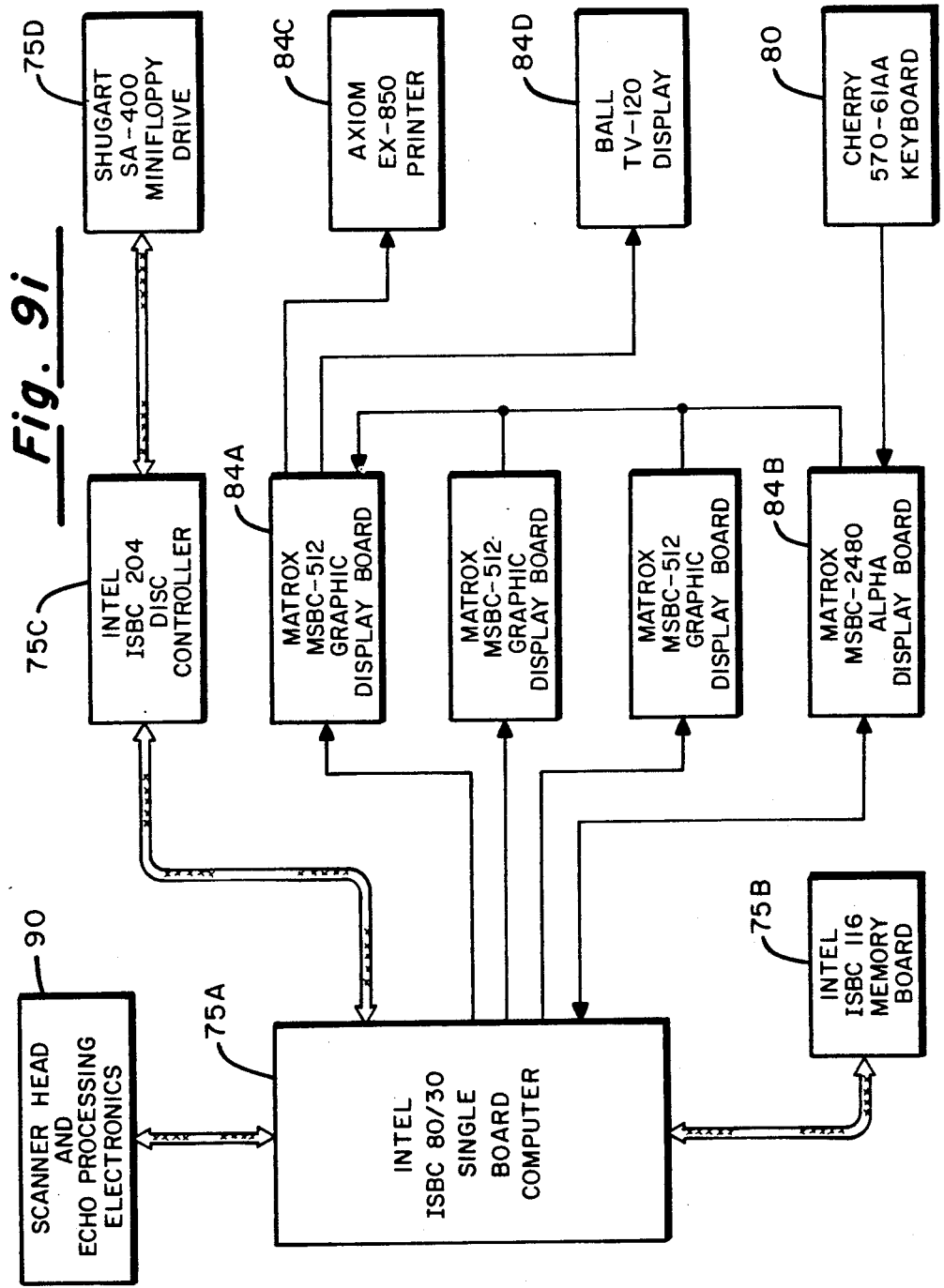

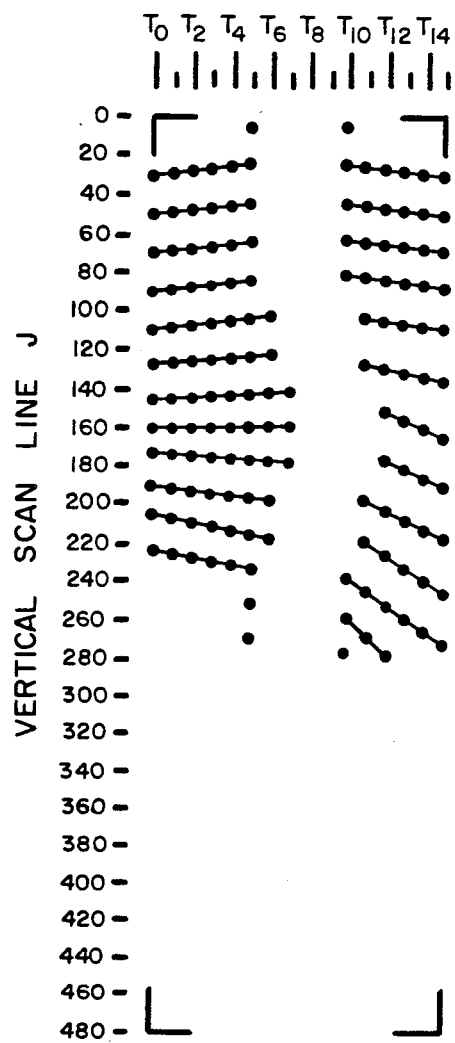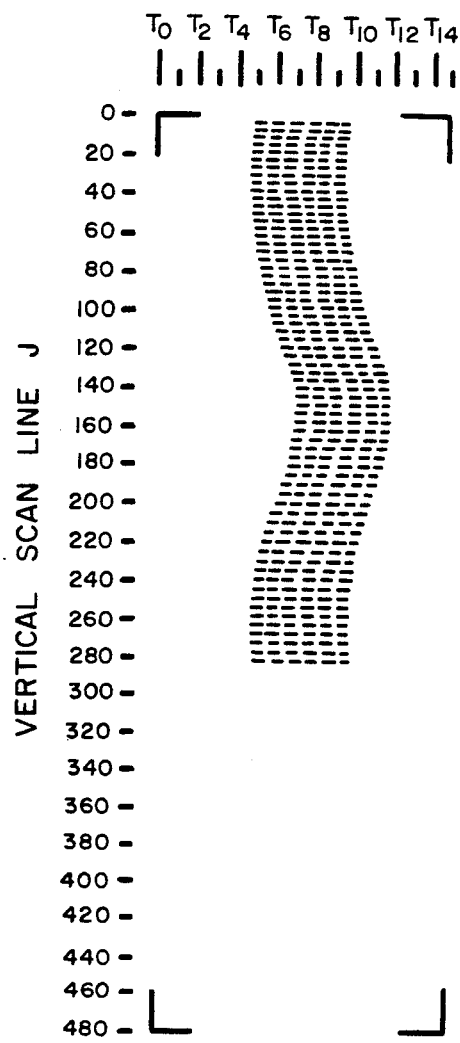
*Fig. 13*          *Fig. 14*

ULTRASOUND IMAGING SYSTEM

APPENDIX CROSS-REFERENCE

This application contains an appendix which is a microfiche appendix of a total of one fiche and fifty-six frames.

REFERENCES TO COPENDING APPLICATIONS

This application contains matter disclosed and claimed in the following copending applications filed on even date with the present application:

ULTRASOUND SCANNING SYSTEM FOR SKELETAL IMAGING, Ser. No. 415,042, by Paul D. Sorenson, Dale A. Dickson, Larry A. McNichols, and John D. Badzinski;

SYSTEM WITH SEMI-INDEPENDENT TRANSDUCER ARRAY, Ser. No. 414,704, by Paul D. Sorenson and Dale A. Dickson;

ULTRASOUND SCANNER WITH MAPPED DATA STORAGE, Ser. No. 415,044, by Paul D. Sorenson and John D. Badzinski; and ULTRASOUND IMAGING SYSTEM FOR SCANNING THE HUMAN BACK, Ser. No. 414,705, by Paul D. Sorenson and Dale A. Dickson.

BACKGROUND OF THE INVENTION

1. Field of the Invention

This invention in general relates to the field of ultrasound imaging, and more particularly concerns a system and method for ultrasound imaging of structures such as the spinal column and ribs, which reflect ultrasound at a variety of angles.

2. Description of the Prior Art

This invention arises out of a project to devise a device that would be useful in the diagnosis of scoliosis. Scoliosis is a disease resulting in the deformity of the spine. The disorder, which is a significant worldwide health problem, is characterized by both lateral curvature and rotation of the vertebrae. The cause of idiopathic scoliosis, which is the most common class of scoliosis, is unknown, but the symptoms generally appear during the developmental years. Failure to effectively treat the disorder in those cases where the curvature progressively grows worse leads to deformity of the torso and potentially, cardiopulmonary distress. Patients are often treated by orthopedic surgeons during the adolescent years of childhood by one or more methods which include external orthotic bracing, spinal fusion surgery, and electrical stimulation (internal and/or external) of the paraspinal muscles.

Presently, the most widely used clinical method employed to diagnose, assess, and track the course of the disease is standard x-ray imaging. Since there are no reliable methods yet available to predict the rate of progression of the disease, the patient is examined on a regular basis. Typically, a child will be subjected to a large number of x-rays over the course of the disease regardless of the treatment modality implemented. In many cases, no treatment is warrented, but the child is x-rayed periodically to verify that the curve has not progressed significantly. It therefore becomes highly desirable to develop a technique of detecting and monitoring scoliosis which will minimize or eliminate x-ray exposure. In recent years, great emphasis has been placed on the need to develop effective, safe methods of screening children in public schools.

Aside from the issue of safety, the x-ray instrumentation currently used does not lend itself optimally to the rapid assessment of scoliosis. For example, just the right contrast must be obtained and then the equipment must be run by a radiological specialist. Further, the orthopedic surgeon must ponder the x-ray and then perform certain geometric operations on the image in order to extract quantitative information regarding the nature of the spinal curvature. Another parameter which is becoming increasingly important to measure is the amount of vertebral rotation which accompanies the lateral curvature of the spine. This is presently difficult to accurately assess using x-ray.

Not many alternative means to x-ray for assessing scoliosis appear in the literature. One method currently under limited evaluation is called the Moire technique. This is an optical photographic technique which detects bilateral nonsymmetry in the surface features of the back. The method employs the principle of interference fringes. The patient's back is photographed through an interference screen or defraction grating. This results in a set of contour-line shadows on the photograph which is indicative of the surface topology of the back. The main shortcomings of this system are two-fold. First, there are no established scientific correlative studies relating visual surface features to spinal curvature. Secondly, the device is primarily aimed at screening rather than the quantitative assessment of the magnitude of the spinal curvature. Thus a system and method with which spinal curvature could be directly measured which can be repeatedly used without damage to a child or other person would be highly desireable.

As mentioned above, the system of the invention for overcoming the problems with the prior art methods of tracking scoliosis features ultrasound imaging. A wide variety of ultrasound imaging systems have been devised, although none of them known to us appear to be particularly suited for the imaging problem at hand. Examples of such imaging systems are disclosed in U.S. Pat. No. 4,242,912, which discloses a system including an array of transducers which are energized in cyclically selected groups, and U.S. Pat. No. 4,252,026, which discloses an ultrasound imaging system which employs a plurality of transducer elements for receiving echoes.

SUMMARY OF THE INVENTION

It is an object of the invention to provide an ultrasound imaging system that is particularly suited for imaging structure which reflects ultrasound at a variety of angles.

It is another object of the invention to provide an ultrasound imaging system that is particularly effective for imaging skeletal structure, and especially the skeletal structure of the back.

If is a further object of the invention to provide an ultrasound imaging system that provides one or more of the above objects in a system that provides data quickly so that it is utilizable in real time by the physician.

It is another object of the invention to provide an ultrasonic imaging system that provides skeletal representations that are accurate, and are easily correlated with established scientific forms.

The invention provides an ultrasound imaging system having a plurality of ultrasound transducers for generating an ultrasound signal, for receiving an ultrasound signal, and for producing an electrical transducer signal representative of the received signal. Preferably, the transducers are in a linear array or in an N×M two-dimensional array where N is the number of transducers in each row and M is the number of transducers in each column, and the centers of the transducers in each row are offset from the centers of the transducers in the adjacent rows. There is a means for providing a range signal representative of the distance of objects interacting with the ultrasound signal, timing means for producing a timing signal, and a means for energizing of the transducers. There is a means for listening for an ultrasound wave being received with at least one of the transducers selected as a listening transducer and for producing a stop signal indicative of an ultrasound wave being received. There is a sequence means responsive to the timing signal and electrically connected to the means for energizing and the means for listening, for selecting a sequence of firing transducers, for causing the means for energizing to fire the selected firing transducers at first determined times, for selecting a sequence of listening transducers and for causing a means for listening to listen to the selected listening transducer during second determined times, the sequencing means also responsive to the stop signal for selecting the next in sequence of firing transducers whenever the stop signal is received, until the firing and listening sequences are completed. The invention also includes means responsive to the electrical transducer signals and the range signals for producing an output representative of the ultrasound signals. Preferably, the sequence of listening transducers include the firing transducer and the transducers adjacent to the firing transducer. Numerous other features, objects and advantages of the invention will become apparent from the following detailed description when read in conjunction with the accompanying drawings.

BRIEF DESCRIPTION OF THE DRAWING

In the drawing:

FIG. 1 shows an imaging system according to the invention with the transducer transport portion of the system in position to image a portion of the patient's ribs and spinal column;

FIG. 8 shows a block diagram of the preferred embodiment of the ultrasound imaging system according to the invention;

FIG. 9a shows the motor control circuit utilized in the embodiment of FIG. 8;

FIG. 9b shows the electronic circuit of the A/D converter for scanner head position utilized in the embodiment of FIG. 8;

FIG. 9d shows the arrangement of FIGS. 9i d.1 and 9d.2 which in turn show the electronic circuitry for the non-linear time-gain amplifier, including the echo discriminator (rf detector and comparator), utilized in FIG. 8;

FIG. 9f shows the electronic circuitry for a second range counter utilized in the embodiment of FIG. 8;

FIG. 9i shows the block diagram for the microprocessor system utilized in the embodiment of FIG. 8;

FIG. 13 shows a display representative of the rib and spinal system formed by connecting the rib and spinal positions determined form the data of FIG. 12;

FIG. 14 shows an alternative display representing a spinal system formed by connecting the boundaries of rib and spine displayed in FIG. 13.

DESCRIPTION OF THE PREFERRED EMBODIMENT

Figure 2:
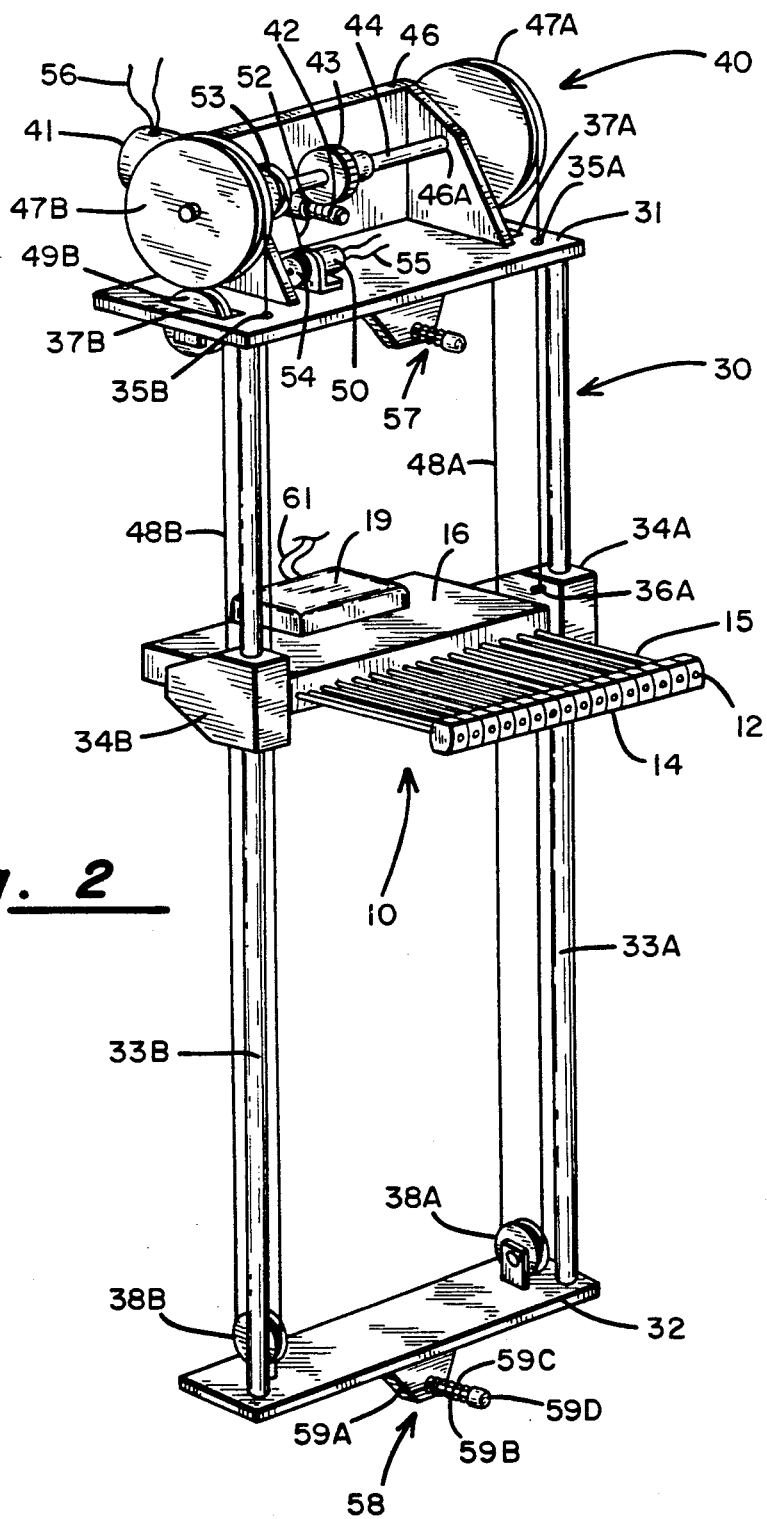
FIG. 2 shows a perspective view of the transducer transport system of FIG. 1.

An exemplary embodiment of an ultrasound scanning system, according to the invention, for skeletal imaging is shown in FIG. 1. The system includes several major subsystems, including a scanner head 10, a transport system 30 for orienting and moving the scanner head in a particular fashion, a microprocessor-based control and display counsole 60, and keyboard terminal 80. The scanner head 10 provides a means of acoustically coupling low-intensity ultrasound energy to the back of the patient 11. The transport system 30 moves scanner head 10 is a straight line between two anatomical landmarks—cervical reference means 31 and sacral reference means 32. Control for the scanning process, the sequencing of the transducers, data processing, record storage, and output of results is provided by microprocessor-base system console unit 60 which is electrically coupled to scanner head 10 via flexible electrical cable 61 and to transport system 30 via electrical cable 62. Keyboard terminal 80, which can be considered to be part of the system control console 60, provides a means of inputing scanner control commands as well as pertinent patient information.

In order to clearly illustrate the invention, the description will contain three parts. First, a brief description of the mechanics of ultrasound will be presented. Second, a detailed description of the structure and electronic circuitry of the preferred embodiment will be given. Finally, a description of the operation of the invention including the method of the invention and the principle features of the invention will be given.

ULTRASOUND MECHANICS

If a mechanical sound wave in an ultrasonic frequency range (typically 1 MHz to 10 MHz) is generated and acoustically coupled to biological tissue, the wave will propagate through the tissue at a velocity determined by the physical properties of the tissue. Reflections or "echoes" will occur whenever the velocity of propagation of the sound wave is altered. Interfaces between different tissue types within the overall biological media, in general, present a change in propagation velocity and hence a portion of the incident energy is reflected. The magnitude of an echo is proportional to the magnitude of the incident energy and the change in velocity at the interface. For example, when ultrasonic energy traveling at 1580 m/s through a layer of muscle tissue encounters bone, the velocity of propagation is increased to 4080 m/s and about 40% of the energy incident on the bone will be reflected in the form of an echo.

Figure 5A:
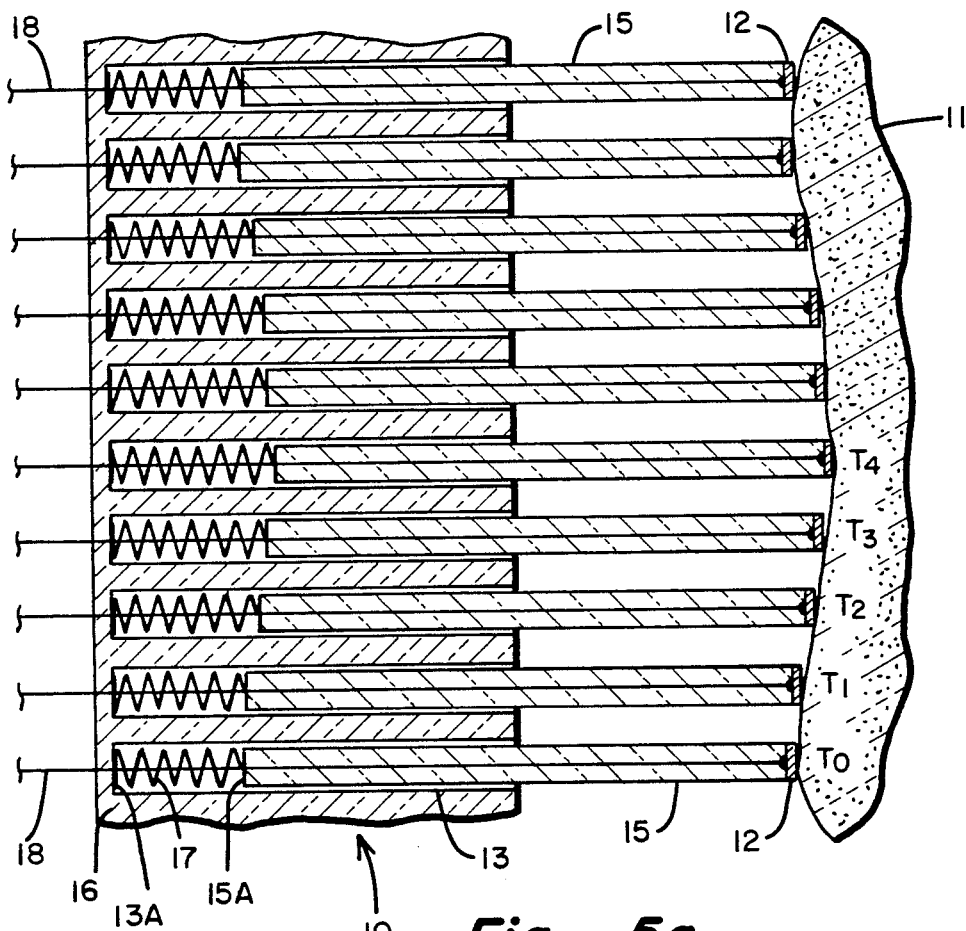
FIG. 5a shows a cross section of the scanner head taken through line 5a–5a of FIG. 3 and showing the transducers pressed against a section of the patient's back.

Low power (typically less than 100 mW/cm$^2$ average) ultrasound may be easily generated by the application of a short pulse of voltage (200 V for 1 $\mu$s typical) to an appropriately constructed piezoelectrical crystal such as 12 (FIG. 5a). Momentary deformation of the crystal 12 ensues and it vibrates for a short period of time at its natural resonant frequency (2.25 MHz for the present embodiment). Consequently, a low intensity mechanical pressure wave or sound wave is set up in the media 11 to which the element is coupled.

Conversely, the presence of an incoming ultrasonic wave front in the form of an echo may be detected because the resulting pressure on the crystal 12 produces a voltage across the crystal 12. Such crystals 12 are called ultrasound transducers and the same transducer is typically employed to both transmit and receive pulses of ultrasonic energy.

By aiming the transducer 12 at a target in particular direction within a defined coordinate system and measuring the time elapsed between the transmission of a sound wave and the reception of an echo from the target it is possible to calculate the distance or range to the target, and subsequently to locate the position of the target within the coordinate system. Further, it is possible to determine certain features of the target (for example surface texture) by analyzing the resulting echo waveform.

In the prior art, medical ultrasound has been employed to examine internal soft tissue organ structures. Such structures generally reflect ultrasound over a narrow range of angles. On the other hand, sharp bony structures, such as the spine tend to reflect ultrasound over a wider range of angles. As ultrasound transducers emit sound waves as they pass over such structures, echoes, in general, will be produced, but due to the complex geometry of the reflecting surfaces, the echoes may not return directly to the launching transducer. The present disclosure will disclose how these important echoes may still be captured. The present disclosure will also disclose how an array of transducers and the sequencing of the firing and listening of transducers under the management of a microprocessing system may be used to perform a specific type of geometric characterization of the spine and ribs.

STRUCTURAL AND ELECTRICAL DESCRIPTION

Figures 3, 4:
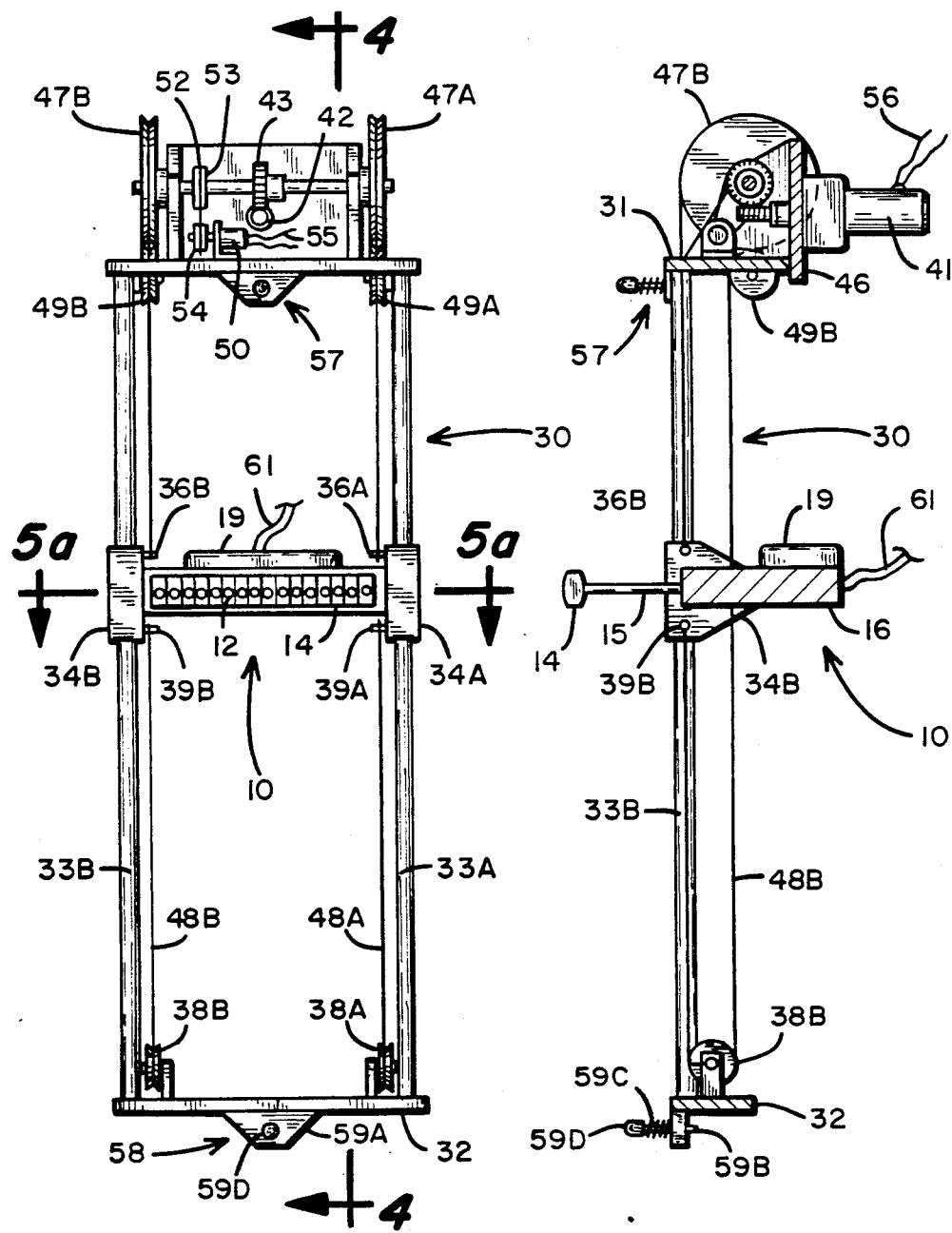
FIG. 3 shows a front view of the transport system of FIG. 2.
FIG. 4 shows a cross-sectional view of the transport system taken through line 4—4 of FIG. 3.

We now proceed to the detailed structural description of the apparatus according to the invention. A perspective view of the scanner 10 and the transport system 30 for moving the scanner head 10 is shown in FIG. 2. A frontal view of the same system is shown in FIG. 3 and a cross section taken through lines 4—4 of FIG. 3 is shown in FIG. 4. FIG. 5 shows a cross section of the scanner head taken through lines 5—5 of FIG. 3. The transducer shoes of FIG. 3 are omitted in FIG. 5a for clarity. All these figures will be discussed together.

Together the scanner head 10 and the transport system 30 provide means for supporting and moving the transducer 12. In the embodiment shown in FIG. 2 there are sixteen transducers such as 12. Each transducer, such as 12, is embedded in a transducer shoe, such as 14, which is attached to the end of a movable plunger, such as 15. The scanner head 10 comprises scanner body 16 having sixteen cylindrical bores, such as 13. Each of the bores 13 is of a diameter just slightly larger than the plungers such as 15, and each of the plungers 15 slide within one of the bores such as 13. Within each of the bores, such as 13, there is a spring such as 17, one end of which seats against the bottom 13A of its respective bore 13 and the other end of which seats against the end 15B of plunger 15 opposite transducer 12. A wire, such as 18, is electrically connected to each of the transducers, such as 12, and extends through the plunger 15 and bore 13 through scanner body 16 into scanner electrical box 19 where they are connected into the transducer electronics (see below) and ultimately to flexible electrical cable 61.

Scanner transport system 30 includes a frame top plate 31 and a frame base plate 32 separated and connected by a pair of scanner head rails 33A and 33B. Rails 33A and 33B pass through a cylindrical bore within scanner head blocks 34A and 34B respectively. The bore blocks 34A and 34B is just slightly larger than the diameter of rails 33A and 33B respectively so that blocks 34A and 34B slide easily on their respective rails. Scanner body 16 is secured to the inner side of blocks 34A and 34B so that the whole scanner head 10 moves as a unit on rails 33A and 33B. The major portions of the drive system 40 for the scanner head 10 is mounted on top plate 31. Drive means 40 includes motor 41 which drives a worm and wheel gear (42 and 43 respectively). Wheel 43 is supported by and locked to axle 44 which is, in turn, supported on frame 46 and turns in bushings 46A and 46B (not shown) in frame 46. Frame 46 is mounted on plate 31 to support the drive system. Grooved drums 47A and 47B are connected to either end of axle 44 and turn with the axle 44. A pair of cables 48A and 48B seat in the grooves of drums 47A and 47B respectively, pass through holes 35A and 35B respectively in top plate 31 and are fastened to pins 36A and 36B set in blocks 34A and 34B respectively. The other end of cables 48A and 48B pass over guide pulleys 49A and 49B mounted in slots 37A and 37B in plate 31, then pass under pulleys 38A and 38B mounted on the base plate 32 and return upward to fasten to pins 39A and 39B secured to blocks 34A and 34B respectively.

Position tranducer 50 is mounted on top plate 31 and is driven by transducer drive belt 52 which rotates about position transducer drive pulley 53 which is secured to axle 44 and pulley 54 which is fastened to the drive shaft of position transducer 50. The position transducer 50 is a potentiometer connected nominally across 0 to 12 volts d.c. (typical operating range 2–8 volts d.c.). As pulley 54 turns, a wiper within the potentiometer 50 moves and produces a voltage proportional to the distance which the scanner head 10 has moved. Wires 55 which carry the output signal of position transducer 50 and wires 56 which carry the input current to motor 41 form flexible electrical cable 62 (FIG. 1).

Located on the transducer support system 30 are means 57 for referencing the ultrasonic transducer position to a cervical reference point and a means 58 for referencing the ultrasonic transducer position to a sacral reference point. Each of these reference means includes a bracket such as 59A which supports a push rod, such as 59B which is mounted in a hole through bracket 59A. A spring 59C seats between one side of bracket 59A and a cap 59D mounted on the end of push rod 59C. Together the reference means such as 57, scanner head 10, the cables such as 48A, drums 47A, axle 44, drive pulley 53, drivebelt 52 and position transducer 50 provide a means for producing a position signal representative of the position of transducer 12.

Figure 5B:
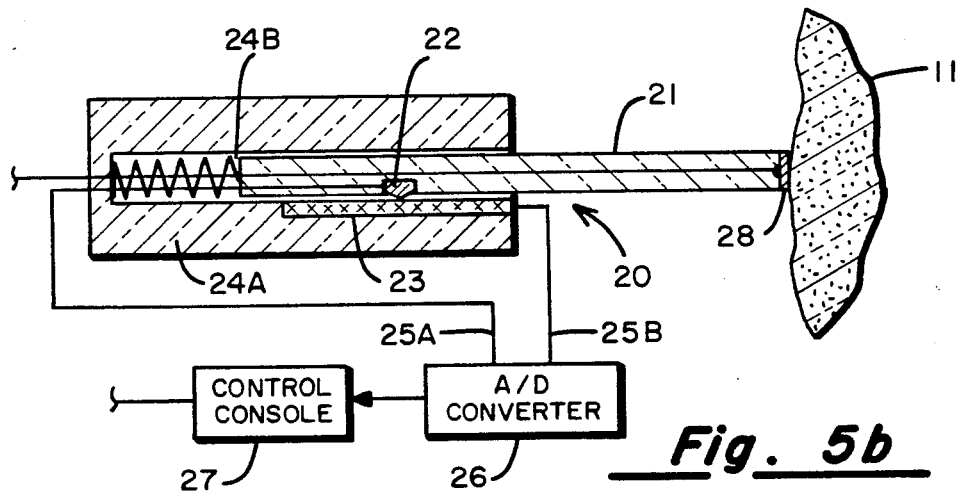
FIG. 5b is a cross-sectional side view of alternative embodiment of the scanner head showing a linear position transducer.

FIG. 5b is a cross-sectional side view of an alternative embodiment of the scanner head. In this figure the transducer shoe is again not shown. This embodiment includes a linear position transducer 20 which produces a signal proportional to the position of plunger 21. Linear position transducer 20 includes a contact 22 secured on the bottom side of plunger 21 and extending a small distance beyond the side of the plunger 21, and a resistance element 23 embedded in scanner body 24A with its surface exposed along a section of bore 24B so that contact 22 moves along resistance element 23 as plunger 21 moves in bore 24B. Wire 25A is attached to contact 22 and wire 25B is attached to one end of resistance element 23 and both wires 25A and 25B are input to an A/D converter 26 to complete a circuit through resistance element 23. The voltage through the linear transducer circuit 20 is proportional to the position of contact 22 on resistance element 23 and thus is a measure of the position of plunger 21 and ultimately of the position of transducer. The A/D converter translates the voltage to a digital signal in a manner similar to that described below. The digital signal is input to the control console 27 for use as will be discussed below.

Note that wires 18 (in FIG. 5a) and 25A (in FIG. 5b) are shown straight only for clarity. In actuality they are coiled in the bore so that they may extend and contract as plungers 15 and 21 move.

Figure 6:
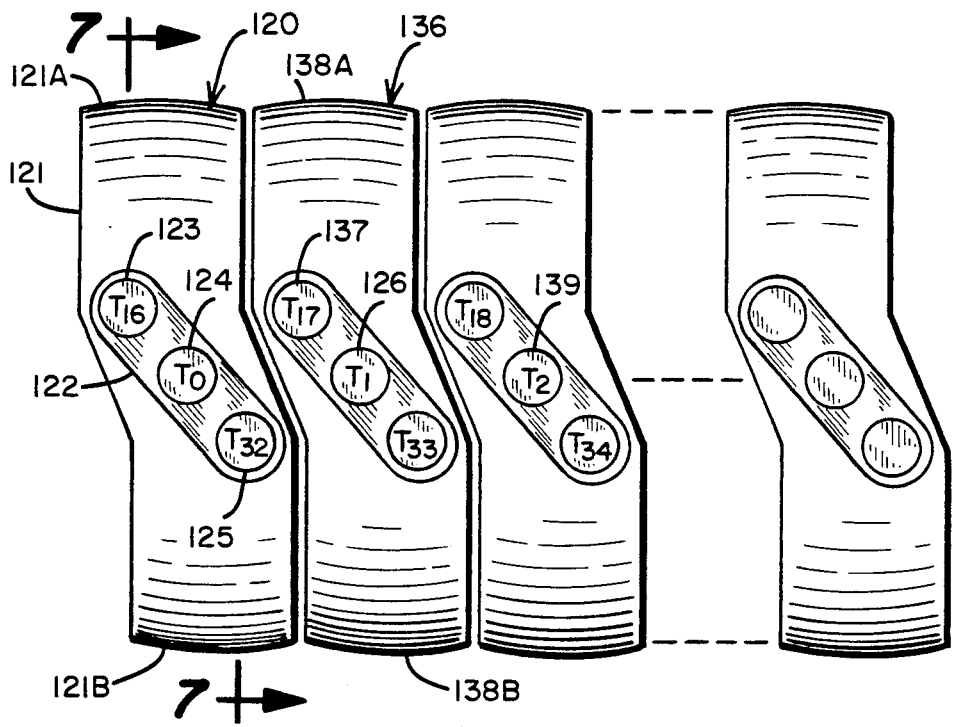
FIG. 6 shows a front view of an alternative embodiment of the transducer head which employs three transducers per transducer shoe.
Figure 7:
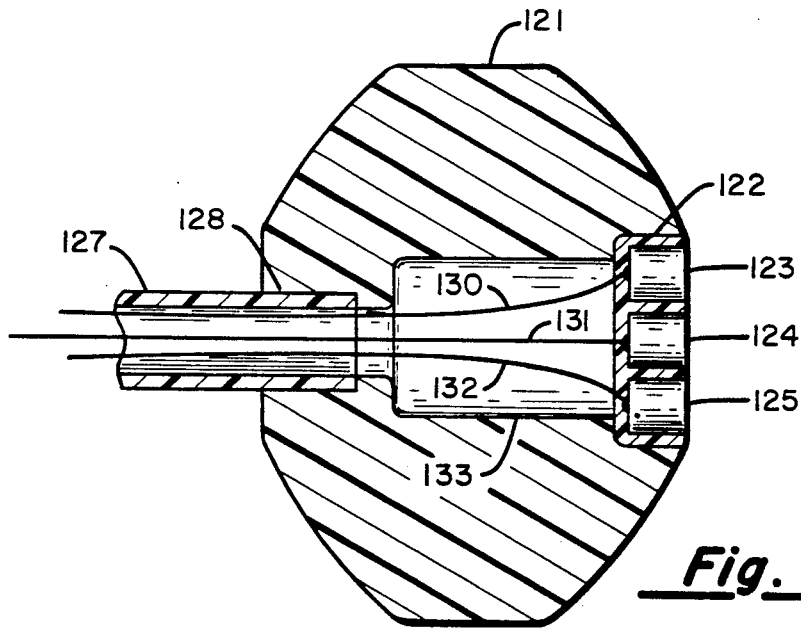
FIG. 7 shows a cross-section of one of the transducer shoes of FIG. 6 taken through line 7—7 of FIG. 6.

FIGS. 6 and 7 show a preferred embodiment of the transducer shoe. FIG. 6 shows a front view of four shoes with the gap indicating additional shoes may be inserted; in the case of the preferred embodiment there are sixteen such shoes. Each shoe, such as 120, includes a shoe body 121, transducer housing, such as 122 in which three transducer crystals, such as 123, 124, and 125 are embedded. Each shoe 120 is supported by a hollowed cylindrically shaped transducer rod 127 which fits into a bore 128 formed in the rear of the shoe body 121. Wires 130, 131, and 132 pass through a hollow 133 formed in shoe body 121 and through rod 127 to connect each of transducers 123, 124 and 125 to the transducer electronics as discussed above. Transducer housing 122 is embedded in shoe 121 at an angle so that there is a slight bit of overlap in the vertical plane between the individual transducer crystals, as for example, between crystal 123 and 124. Further, each individual shoe, such as 120, has the top portion of the shoe, such as 121A, offset from the bottom portion of the shoe, such as 121B, so that the top portion of each adjoining shoe overrides the bottom portion of the next shoe, as for example, top portion 138A of shoe 136 overrides the bottom portion 122B of shoe 120. The overriding is such that the last transducer in one shoe has the same overlap with the first transducer of the next shoe as the individual transducers in each shoe have, as for example, transducer crystal 125 in shoe 120 overlaps with transducer crystal 137 in shoe 136. The advantages of this arrangement of transducers and transducer shoes will be discussed below.

FIG. 8 shows a block diagram of the electronic system utilized in the embodiment of the invention shown in FIG. 1. The electroniccs included in scanner head 10 is enclosed in the dashed rectangle. In this diagram the transducers are indicated as $T_0, T_1, T_2, \ldots T_I \ldots T_{N-2}, T_{N-1}$ for purposes of the generalized discussion below. In this embodiment there are sixteen such transducers and thus, N is equal to 16. In the embodiment using the shoes of FIGS. 6 and 7, N is equal to 48. The transducer driver and receiver circuitry 71 delivers signals to and receives signals from the ultrasonic transducers 70. One of sixteen selector circuitry 72 (or one in forty-eight circuitry for the embodiment of FIGS. 6 and 7) receives signals from the microprocessor system 75 and in turn, applies signals to the transducer drivers and receiver circuitry 71. Received signal multiplexer 73 receives the signals derived from the reflected ultrasonic waves from the transducer driver and receiver circuitry 71. A signal from the microprocessor system 75 is applied to received signal multiplexer 73 to inform it which signal should be recognized. The signals recognized by the received signal multiplexer 73 are passed to the linear preamp 74 and, after amplification, proceed on to the nonlinear time-gain amplifier 76. The doubleline 77 indicates a mechanical linkage between the motorized mechanical transport system 78 and the ultrasonic transducers 70. As discussed above, there is also a mechanical linkage between motorized mechanical transport system 78 and position transducer 79. The signal from position transducer 79 is applied to position A/D converter 81 and the digital output from the position A/D converter is applied to the microprocessor system 75. The microprocessor system 75 applies a clock signal and a start signal to range counters 82. The output of the nonlinear time gain amplifier 76 is applied to echo discriminator 83 and when an echo is detected a signal is applied to the stop input 83C of range counters 82. The signal from the range counters is applied to the microprocessor system 75. In this embodiment the microprocessor 75, the range counters 82, and the echo discriminator 83 together comprise a means for providing a range signal representative of the distance of objects interacting with the ultrasound signal. The microprocessor system 75 provides an output to the display system 84. High-speed A/D converter and memory buffer system 85 is an optional part of the system which will be discussed below. This system 85 receives signals from nonlinear time-gain amplifier 76 and microprocessor system 75; these signals are indicated by dotted lines to indicate they are optional. The signal from high-speed A/D converter and memory buffer system 85 is applied to microprocessor system 75.

FIGS. 9a through 9h show details of the circuitry of each of the portions of the circuitry shown in FIG. 8. With the exception of the time-gain amplifier, the particular elements of the subcircuits are for the most part conventional and those skilled in the art will be able to develop such circuits and alternatives to such circuits from the description given and standard electronic literature. However, the various parts used and sources for those parts will be presented in order to fully elucidate the construction of the invention.

Figure 9C:
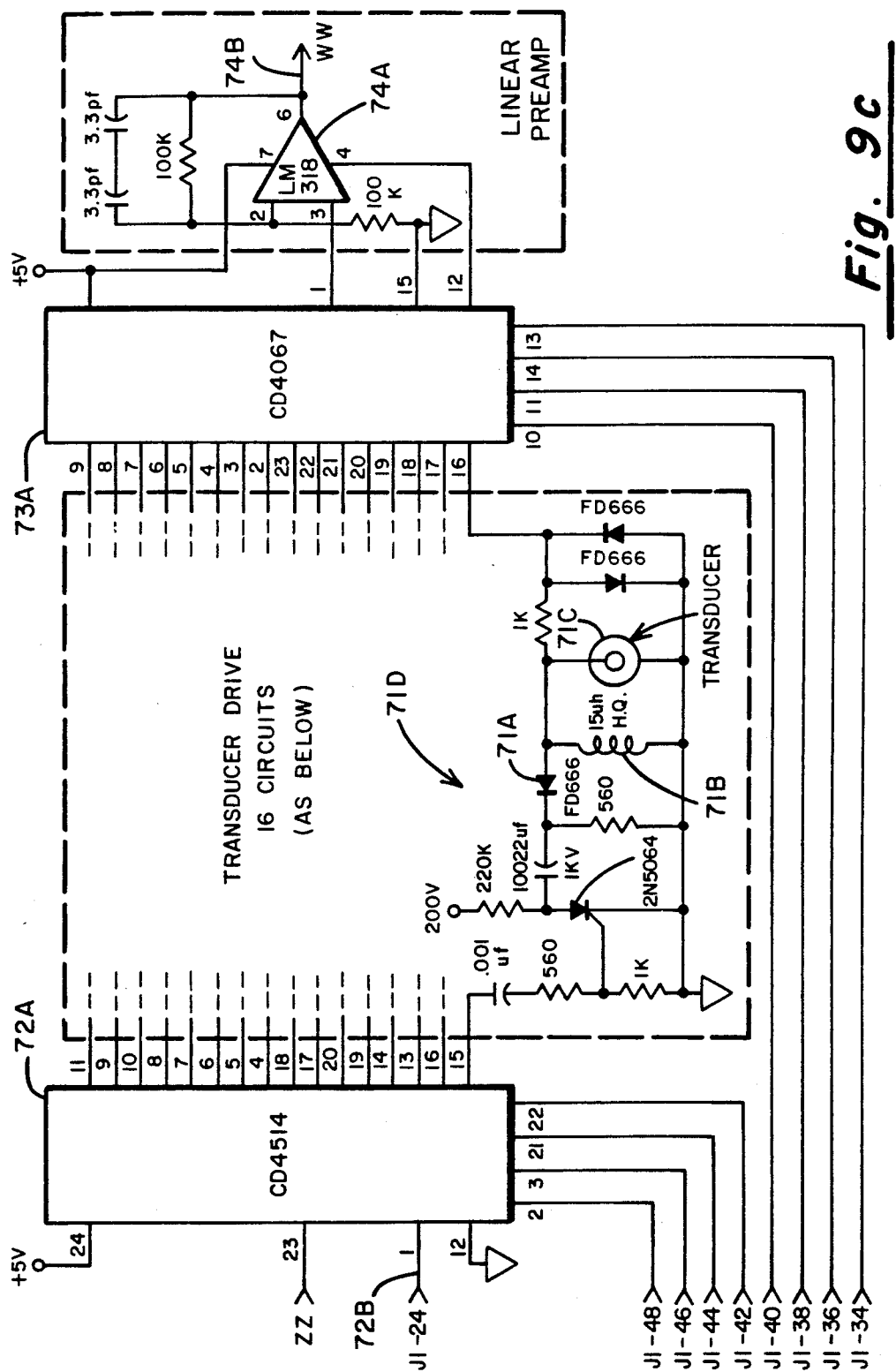
FIG. 9c shows the electronic circuitry for the transducer drivers and receivers including the 1 of 16 selector, the received signal multiplexer and the linear preamp utilized in the embodiment of FIG. 8.

The motor control circuitry is shown in FIG. 9a. In this figure, and the subsequent figures showing electronic circuitry, standard electronic symbols for the various circuit elements are used. Each of these elements will be pointed out in the first figure in which they are encountered. In FIG. 9a, a resistor is shown at 78A, with the value of the resistor given in ohms alongside the resistor. A transistor is shown at 78B, with the standard trade designation for the transistor type given alongside the transistor (MJ4032 for transistor 78B). A capacitor is shown at 78C with the value of the capacitance, 0.01 TM f, given next to the capacitor. A field effect transistor (FET) is shown at 78D, with the standard trade designation of the FET type, 2N6660 given next to the FET. The symbol at 78E, shaped like the tail of an arrow, indicates a connector. The number next to the connector symbol, such as J1-30 at 78E, indicates where the connection is to be made. For example, the J1-24 at 72B in FIG. 9c is connected to the J1-24 connection at 76A in FIG. 9d. Furthermore, all such symbols which begin with a J1, J2 or J3 designation refer to standard connection points on an ISBC 80/30 single board computer microprocessor system made by the Intel Corporation, 3065 Bowers Avenue, Santa Clara, Calif. 95051. Triangles, such as 78F, indicate a digital signal ground, while small circles, such as at 78G indicate a plus or minus voltage connection. The voltage is given next to the circle, either as a plus or minus numerical voltage or as $Vcc_1$ or $Vcc_2$ which indicate positive DC power supply voltages. Normally $Vcc_1$ would be set at +12VDC and $Vcc_2$ would be set at +5VDC. The higher voltage ($Vcc_1$) runs the motor while the scanner head is being raised or returned to the ready position while the lower voltage $Vcc_2$ is switched to when the scan is being conducted. This saves time during the return of the scanner head. The circuitry for the position A/D converter for the scanner head position is given in FIG. 9b. The large rectangle 81A is a analog-to-digital converter chip such as that made by Analog Devices, Inc., Route 1, Industrial Park, P.O. Box 280, Norwood, Mass. 02062. The designation for this chip and other chips used in the electronics is shown in the rectangle. At 81B a variable resistance is shown, with the maximum value of the resistance (100 Kohms) given next to the symbol. The symbol at 81C indicates a potentiometer with the maximum value of the resistance of the potentiometer (20 Kohms) given next to the symbol for the potentiometer. The 1 Kohm potentiometer at 81D is the potentiometer within the position transducer 50 in FIG. 2.

The electronic circuitry for the one of sixteen selector, the transducer drivers and receivers, the received signal multiplexer and the linear preamp are shown in FIG. 9c. The one of sixteen selector circuitry is essentially contained in integrated circuit chip 72A. This is a standard integrated circuit chip which may be purchased, for example, from RCA Solid State, Box 3200, Summerville, N.J. 08876. Symbol 71A represents a signal diode, with the standard trade designation for the diode given next to the symbol. 71B is an inductance with the value for the inductance given next to the symbol. Transducer 71C is a 2.25 MHz transducer produced by Harrisonics of Stamford, Conn., 06902. Received signal multiplexer is also essentially contained in an integrated circuit chip 73A with the standard trade designation number given on the chip. Symbol 74A in the linear preamp circuit represents an operational amplifier, such as that produced by National Semiconductor Coporation, 2900 Semiconductor Drive, Santa Clara, Calif. 95051. The transducer drive and receiver circuitry shown at 71D is reproduced sixteen times, once for each transducer in the preferred embodiment and each of the sixteen circuits are connected between selector 72A and multiplexer 73A as indicated by the dotted lines in the drawing. The WW designation given at point 74B indicates a wire connection to the terminal labeled WW at 76C in FIG. 9d.1. Likewise, other points with double lettered designations elsewhere in the drawings indicate wire connections between identically labeled points.

The nonlinear time-gain amplifier and echo discriminator is shown in FIGS. 9d.1 and 9d.2. The two figures should be placed side-by-side as shown in FIG. 9d and are connected along line 76A. In FIG. 9d.1 the only new symbol introduced is shown at 76B. This is a dual gate FET, and the standard trade designation for the FET is given just above the symbol. The echo descriminator circuitry is shown in FIG. 9d.2. This includes an RF detector and a comparator as shown. The three transistors and diode indicated by 83A are formed in a single standard chip with the trade designation CA3146. All other elements in the circuits have been previously described.

Figure 9E:
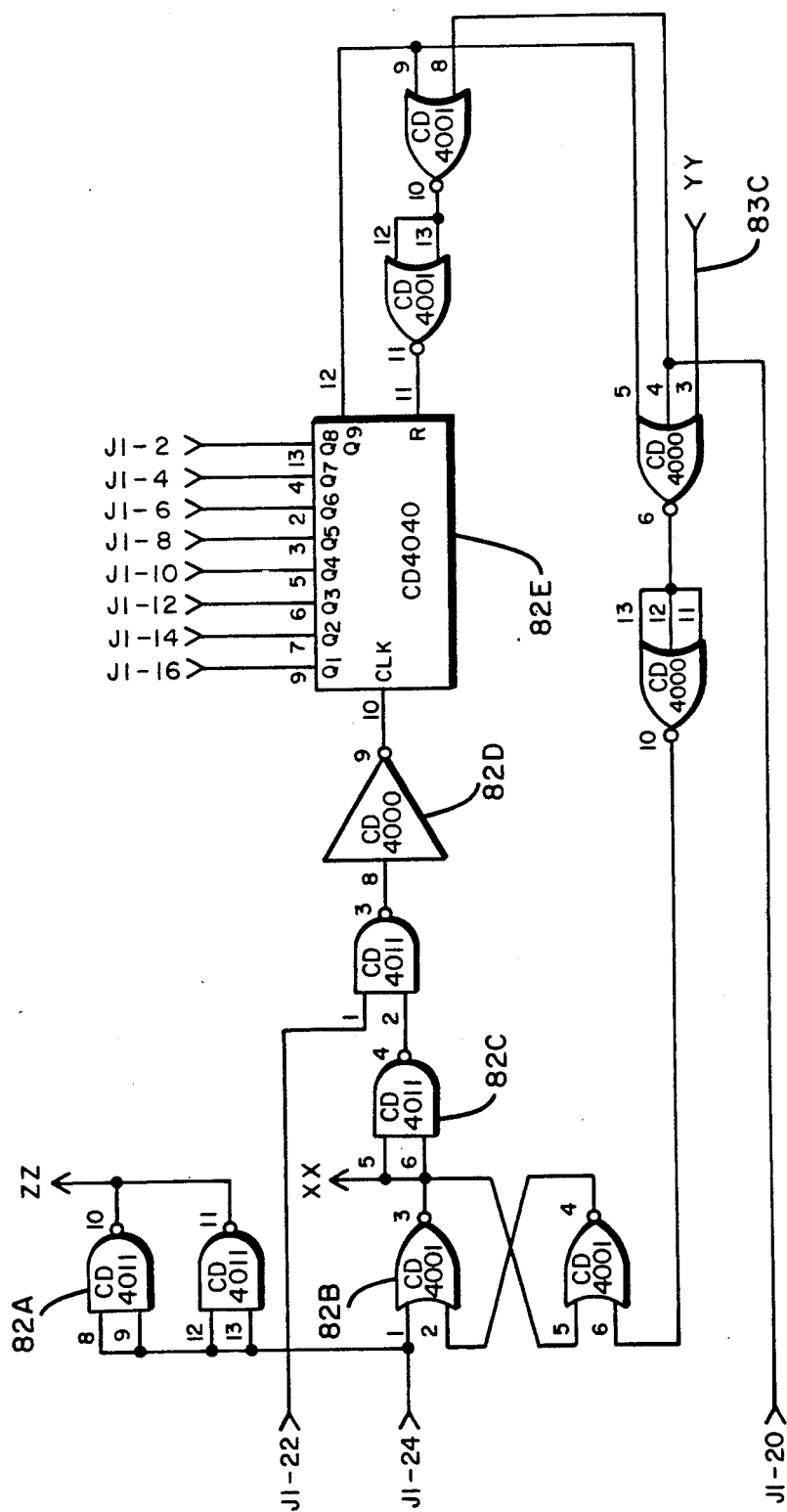
FIG. 9e shows the electronic circuitry for a range counter utilized in the embodiment of FIG. 8.

The first of two range counters is shown in FIG. 9e. This circuit includes four NAND gates, such as 82A, six NOR gates, such as 82B, and an inverter shown at 82D. The four gates designated CD4011 are contained in a single integrated circuit package, as are the four gates indicated by the designation CD4001 and the two gates and inverter indicated by the designation 4000. 82E is a binary counter, with the standard trade designation indicated on the drawing.

The circuitry for a second range counter is given in FIG. 9f. This circuitry includes four AND gates 82F located on a single standard chip. Element 82G is a flip-flop, with the standard designation for the flip-flop given on the drawing. The OR gates, such as 82H are also located on a single standard chip.

Figure 9G:
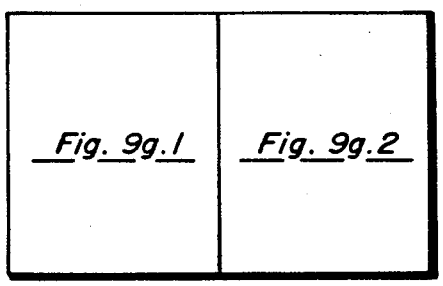
FIG. 9g shows the arrangement of FIGS. 9g.1 and 9g.2 which, in turn, show the electronic circuitry for the high-speed A/D converter and memory buffer system utilized in the embodiment of FIG. 8.
Figure 9H:
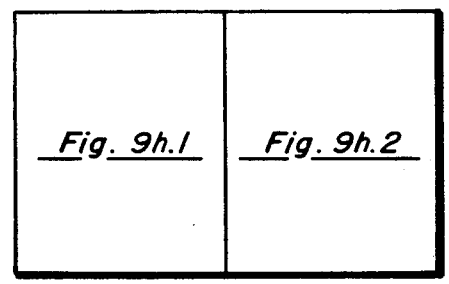
FIG. 9h shows the arrangement of FIGS. 9h.1 and 9h.2 which, in turn, show the electronic circuitry for the control logic for data expansion which is part of the high-speed A/D converter and memory buffer system utilized in the embodiment of FIG. 8.

The circuitry for the optional high-speed A/D converter and memory buffer system is shown in FIGS. 9g.1 and 9g.2. These figures should be arranged as shown in FIG. 9g and when this is done, the connections between the two parts of the circuitry along line 85A is clear. Symbol 85R indicates an analog signal ground. Digital signal grounds and analog signal grounds are maintained separately in the system. The principal parts of this system include the A/D converter 85B, model TDC1007PCB manufactured by TRW, Inc. 10880 Wilshire Blvd., Los Angeles, Calif. 90024 and the model TC1006 high-speed shift registers, such as 85C, also manufactured by TRW, Inc. Symbol 85D represents a standard type BNC connector. In FIG. 9g.2, 85E is a high-speed D/A converter built by TRW (model TDC1016), and 85F is an operational amplifier with the standard designation LM10 such as may be purchased from National Semiconductor Corporation at the address given above. The control logic for utilizing the high-speed A/D converter and memory buffer system in the data expansion process (which will be discussed below) is shown in FIGS. 9h.1 and 9h.2. These two drawings should be arranged as shown in FIG. 9h and when this is done the electrical connections between the two figures along line 85H is evident. In FIG. 9h.1 the triangles 85I are SN7407 drivers, such as those available from Signetics Corporation, 811 E. Arques, P.O. Box 9052, Sunnyvale, Calif. 94086. The arrow heads, such as 85j indicate connections to other points in the drawing with the same designation (for example, connector 85J connects to the CL5 connector 85G in FIG. 9g.2). The arrow head indicates the direction of signal flow. Rectangle 85K represents a 93L10 type synchronous four-bit decade counter, such as that available for National Semiconductor Corporation at the address given above. 85L is a 10 MHz crystal available from International Crystal Mfg. Co., Inc., 10 G North Lee St., Oklahoma City, Okla., 73102. Rectangle 85M is a type CD40103 counter and 85N is type CD4098 dual monostable multivibrator both of which are available from RCA Solid State. FIG. 9h.1 also contains a series of switches such as 85P, which are conventional single-pole, single-throw switches. The circuit of FIG. 9h.2. contains four type 8216 four-bit bidirectional bus drivers, such as 85Q, available from Intel Corporation, 3065 Bowers Avenue, Santa Clara, Calif. 95051.

The block diagram of the microprocessor and display system is shown in FIG. 9i. The heart of the system is an Intel 8085 processor chip incorporated on an Intel ISBC 80/30 single board computer 75A, and an Intel ISBC 116 memory board 75B. This computer system is connected with the scanner head and echo processing electronics 90 as discussed above. For data storage, computer 75A communicates with Intel ISBC 204 disk controller 75C which, in turn, communicates with a Shugart SA-400 mini-floppy drive 75D, available from Harold E. Shugart Company, Inc., 1415 Gardena Avenue, Glendale, Calif. 91204. The display system includes three Matrox MSBC-512 graphic display boards, such as 84A, a Matrox MSBC-2480 alpha display board 84B, an Axiom EX-850 printer 84C, and a Ball TV-120 display 84D. The Matrox display boards can be obtained from Matrox Ltd., 2795 Bates Rd., Montreal Quebec, Canada; the Axiom printer is available from Axiom Coporation, 5932 San Fernando Road, Glendale, Calif. 91202; and the Ball display is available from Ball Electronic Display Division, P.O. Box 43376, St. Paul, Minn., 55164. The display boards, such as 84A and 84B receive inputs from the computer 75A and communicate with each other (arrows). The Alpha display board 84B receives input from the keyboard 80 and applies a signal to computer 75A. Keyboard 80 is a Cherry 570-61AA keyboard available from Cherry Electrical Products Corporation, 3625 Sunset Avenue, Waukegon, Ill. 60085. The system just described, including computer 75A, Memory 75B, controller 75C, display boards, such as 84A and 84B, minifloppy drive 75D, printer 84C, TV display 84D and keyboard 80, when programmed with the software described below, comprise a means responsive to the range signal and the position signal for identifying signals indicative of skeletal structure and for producing an output representative of skeletal structure.

The materials out of which the invention is constructed are, for the most part, obvious from the functions performed: however, these will be briefly described for completeness. Referring to FIG. 2, rails 33A and 33B are preferably made of stainless steel, while plates 31 and 32 and frame 46 are made of aluminum, although any suitable metal or hard plastic material may be used. Wheels and pulleys, such as 47A, 49A, 38A, 53 and 54 may be made of a machineable plastic such as Teflon ®, although any other suitable plastic, metal or other material may be used. Likewise, blocks 34A and 34B and the transducer housings, such as 14 and 121, may be made of Teflon ®, or similar plastics, fibers or metals. Rods, such as 15 and 127, the scanner head bodies, such as 16, and gears, such as 43 and 42, may be made of brass or any other suitable metal or plastic material. Springs such as 17 and 59C, as well as cables such as 48A may be made of stainless steel or any other suitable metal, compressed fiber, etc. Bracket 59A and rod 59B may be made of aluminum, Teflon ® or similar metal or plastic while tip 59D may be made out of rubber, silicone rubber, or other plastics, fibers, etc. The transducer elements such as 12 and 123 may be made of barium titanate (referred to as K-85 ceramic by Harrisonics, Inc.). Resistance element 23 may be made of carbon or any other suitable resistor material.

FEATURES AND OPERATION

To perform a typical back scan a start command is entered via the console keyboard 80. The transport motor 41 elevates the scanner head 10 to the top of the transport rack 30. The transport rack 30 and scanner head 10 are then appropriately oriented on the back 11 of the patient (the patient may be in the standing or prone position) with the cervical reference point 31 and the sacral reference point 32 contacting two well-known palpable anatomical landmarks of the spine such as C-7 and the sacral crest or coccyx. The procedure of aligning the upper and lower reference points 31 and 32 of the transport rack 30 with the upper and lower landmarks of the spine also places the transducers 12 of the scanner head 10 in positive contact with the skin on the back 11 of the patient.

Following a momentary delay, the ultrasound transducers 12 in the scanner head 10 begin to sequentially emit pulses or bursts of ultrasound energy. For example, suppose that the "N" number of transducers in the array 70 (FIG. 8) are numbered from left to right as $T_0, T_1, T_2 \ldots T_I \ldots T_{N-2}, T_{N-1}$, where I is the number of any arbitrary transducer in the array. $T_0$ first acting as an acoustic generator or transmitter emits a short pulse of sound or is said to be "fired". Immediately thereafter, $T_0$ is switched to a receiving mode. As the sound energy propagates through the tissues of the back, the interfaces of various tissue layers cause some sound energy to be reflected in the form of echoes. $T_0$, therefore, listens for a prescribed time period and detects any echo in this "window" of time. If no echo is heard in this "window" of time, then $T_0$ fires again and $T_1$ listens for another prescribed time period. If no echo is heard in this "window", then in the simplest embodiment the listening sequence for $T_0$ terminates. In other embodiments $T_2$, then $T_3$ and so on may listen for prescribed periods. However, generally a sequence that terminates at a relatively nearby transducer to $T_0$ is preferable. The echo signals are processed in a prescribed fashion by the scanner head electronic module and by the system console as described in detail later. $T_1$ then fires and begins listening and if no echo is heard $T_1$ fires again and $T_0$ listens, then $T_1$ fires and $T_2$ listens, and so on until $T_{N-1}$ has fired and the last listening transducer in the listening sequence for $T_{N-1}$ has listened. Following completion of this firing and listening sequence, the process is repeated for N transducers in periodic fashion.

The primary concept being taught through this implementation is that a bony structure (target) with irregular geometry may lie directly in the ultrasonic incident beam path of the firing transducer, but that an echo containing important information about the target may not return directly to the firing transducer. Similar echoes may be generated by repetitive operation of the designated firing transducer and a subsequent search is made for the first listening transducer which is appropriately capturing the off-axis echoes.

Coincident with the transmitting and receiving activity of the transducers, the scanner head 10 moves mechanically away from the cervical reference point toward the sacral reference point. The "field" over which the transducer array scans has dimensions of "X" units wide by "Y" units in length. The computer software is configured such that a memory matrix is defined with "J" referring to rows and "I" to columns. The number of columns corresponds directly to the number of transducers (N) in a row across the scanner head 10. N will be set equal to 16 for purposes of example. The number of rows is equal to a selected number of equal subdivisions (J) in the length (Y) of the scan field. The number of rows will be selected as 480 for further illustration. The scan field may then be represented by a (J, I) matrix of 480×16 or 7680 discrete points. In general, a short burst of ultrasound energy is introduced at least once in methodical fashion at each one of these points in the field of scan and the resulting echo pattern or echo signature is analyzed at each point.

At each point in the field of scan, any echoes occurring are discriminated for selected features by an echo discriminator 83. Calculation of the range or distance between the transducer face and the relevant anatomical structure which produced a discriminated echo at a particular (Y, X) coordinate is performed. Each piece of range information is stored in the corresponding element in the (J, I) memory matrix. Range then becomes a third dimension and is directly related to "Z", the dimension of depth into the back at which the tissue interface producing the discriminated echo is located.

The ramification of this scanning process is that following the application of a one pass linear scan down the back there are potentially 7680 numbers contained in a memory map which may be subsequently rapidly processed to render information on the geometrical relationships between the various components of the dorsal skeletal system.

One important use of this information is to determine the presence or absence of abnormal lateral curvature of the spine (scoliosis) and, further, to automatically assess the severity or "degree" of such abnormal curvature. This is made possible by constraining the transducer array 70 to move in a well defined manner, namely a straight line, between the cervical and sacral reference points. The lateral curvature of the spine may then be referenced to a straight line drawn between these two points–two points through which the spine must pass regardless of its geometry between these two points.

Integrated into the design of the system console 60 are means of visually or graphically communicating results. These means include a cathode ray tube (CRT) 65 and a graphic paper printer 84C to produce a hard copy of any image appearing on the face of the CRT 65. Also included in the scanner console 60 is a "mini-floppy" magnetic disc system 75D. This facilitates the storage of clinical results on a large number of patients combined with patient history information. Acquisition, retrieval and management of all data is facilitated by fingertip control at the console keyboard 80.

Before proceeding with a discussion of the configuration and operation of the ultrasonic scanning system it is appropriate to discuss the features of the scanner head 10 and the mechanical system 30 which supports and transports the head. The concept of the scanner head 10 is perhaps best illustrated by FIGS. 3 and 5. One unique feature of this system is that the individual transducer elements 12 are affixed to plungers 15 which have one degree of freedom of movement, but may move independently of one another. Each plunger/transducer combination is spring loaded within a common housing 16 to all plungers 15 such that when the assembly 10 is pressed against the back of a patient each transducer 12 provides positive compression against the skin 11. As the scanner head 10 is then moved over a complex plane of body curvature such as the human back each transducer 12 independently tracks the curvature such that positive acoustic coupling is maintained for each active element in the scanner head 10.

Also shown in FIG. 2 and in FIG. 7 is the detail of the transducer shoes 14 or 121 which are contoured assemblies into which the transducer elements 12 fit. Transducer shoes are not shown in FIG. 5 for clarity. The shoes 14 or 121 prevent the conventional transducer elements from gouging into the skin 11 of the patient as the scanner head 10 moves. The shoes 14 or 121 greatly alleviate this discomfort.

An embodiment in which a multitransducer element assembly is employed is illustrated in FIGS. 6 and 7. In this example, three elements, such as 123, 124 and 125, are mounted on the tip of each plunger 127, or plunger 15 of FIG. 2. Thus, the scanner head 10 becomes an array with three rows (rather than one row) of transducer elements.

The implications and advantages of three rows of transducer elements will be discussed later when the Multireceiver mode of transducer operation is described.

The mechanical transport system for moving the scanner head down the back is illustrated in FIGS. 2, 3 and 4. Note that the system implemented employs a servo motor 41 and gear reduction (within motor housing) to turn a set of cable drums 47A and 47B. The drums cause steel cables 48A and 48B to move. The scanner head 10 is attached to the cables 33A and 33B such that movement of the cables causes the scanner head 10 to slide either up or down the transport side rails 33A and 33B at a rate determined by the speed of motor 41.

The linear position transducer 20 shown in FIG. 5b may be used in combination with the plunger systems described above. In those embodiments which employ linear position transducer 20, one such linear position transducer 20 is an integral part of each independent plunger 15. The output of the linear transducer is used to make correction in the computed range values as shall be described below.

A number of alternative transporters for the scanner head may be employed, for example a servo motor and gear drive which rotate a long screw shaft positioned midway between the transport side rails 33A and 33B. The screw shaft may be attached via a mating threaded collar to the rear of the scanner head 10. Thus, rotation of the screw shaft would facilitate movement of the scanner head along the side rails.

Still another alternative method of scanner head transportation is to mount a set of wheels on the transducer array assembly. The transducer array 70 and wheel assembly would be pressed against the back and moved manually down the back. The wheels would serve to convert angular rotation of the wheels to linear distance traveled down the back by the transducer array.

A block diagram of the scanning system is shown in FIG. 8. As discussed above, the system is microprocessor-based. The specific microprocessing and display system is shown in more detail in FIG. 9i. The console electronics may be mounted on nine printed circuit boards which insert into console 60 from the rear.

The central processing unit chosen was the Intel 8085 processor chip incorporated on an Intel ISBC 80/30 single board computer. This in itself is a relatively powerful 8-bit microcomputing system containing 4K of read only memory (ROM) and 16K of random access memory (RAM). In addition, an Intel ISBC 116 memory board was included to increase the RAM by 16K. In the discussion which follows concerning the system operation, it is emphasized that all activity is under software control. Software design was, therefore, an intimate part of the overall system design. Broadly speaking, the software may be categorized as operational software or data processing software. Operational software includes all the necessary computer instructions required to control the scanning operation, acquire necessary raw echo data, and store this data in memory. Data processing software includes those computer programs which operate on the raw data to provide numerical and/or graphical characterization of the results. Reference to commands or instructions implies computer instructions implemented via the microprocessor.

The graphics or display system is configured in such a manner that the face of the 12 inch CRT 65 may be characterized as a dot matrix of 512×512 discrete dots each of which may be selectively either lighted or not lighted. This is particularly well suited to this application because data in matrix form may set up so that it may be mapped into a corresponding field on the CRT 65. In addition, the system provides the capability of an eight-level grey scale in the image, i.e. each dot, when turned on, may be set at one of seven levels of light intensity. This was facilitated by interfacing commercially available Matrox MSBC 512 graphics printed circuit cards 84A with the Intel ISBC 80/30 system, as indicated in FIG. 9i. In addition, a Matrox MSBC 2480 board 84B was added for the generation and display of alphanumeric symbols. The system also incorporates an Axiom EX-850 Video Printer 84C so that any image on the face of the CRT 65 may be turned into hard copy at the touch of a button. This particular video printer, however, will not reproduce intermediate levels of grey-scale.

Under processor control any one or any combination of the ultrasonic transducers in the array 70 may be selectively chosen to emit or receive sound energy. The scanning system is operated in a data acquisition mode called Multireceiver. This mode is designed to enhance the probability of capturing target echoes and it will be discussed in greater detail later.

Simultaneously with the launching of a sound wave, a set of one or more range counters 82 are started. The rate of count is controlled by the microprocessor system clock and is approximately 1.2 MHz in the embodiment described. As echoes are received by the designated receiving transducer, this reflected sound energy is converted to a very low level analog voltage with a fundamental frequency equal to the fundamental frequency of the launched sound wave (2.25 MHz). After passing through the multiplexer and receiver blocks 73, this analog echo signal is amplified by a factor of 2 to 5 by the linear preamplifier 74.

The preamplifier is followed by a custom-designed nonlinear time-gain amplifier 76 which has a number of controllable parameters. The details of this circuit and its features will be explained further below. The time-gain amplifier 76 provides a signal gain which increases with time. The time reference for the initiation of this specialized amplification process is keyed from the command to launch a sound wave. An an initial sound wave propagates away from the transducer of origin through the body tissue, it dissipates or is attenuated. Likewise, any reflected energy (echo) is similarly attenuated in the return path. Therefore, since we wish to discriminate echoes on the basis of amplitude, the philosophy in designing the time-gain amplifier is to compensate for sound energy losses in tissue with respect to time.

The gain compensated echo signal is now fed to the echo discriminator block 83. On the front end of the echo detector is an RF detector or full wave envelope detector (FIG. 9d. 2). The purpose of this detector is to remove the high frequency (2.25 MHz fundamental frequency plus harmonics) components from the signal. This results in a signal which is the envelope of the echo signal. This echo profile or echo pattern, therefore, in general, consists of a series of pulses, the amplitude and time position of which contain information about the various tissue interfaces and the distance or depth in the overall tissue aggregate at such interfaces reside.

Following envelope detection, the echo profile signal is fed into a voltage comparator circuit (FIG. 9d.2). The nature of the comparator circuit is such that when and only when an input signal exceeds a selected voltage amplitude, the comparator outputs a well-defined voltage pulse. The output of the comparator provides a "stop" signal for the range counter (FIG. 9e). The echo detection algorithm is designed such that the first echo in time to exceed a preselected amplitude is detected and used to stop the range counter (FIG. 9e).

The relative position of the scanner head 10 is monitored by a position transducer 79 (potentiometer 50 connected to the motor drive system) which generates a DC voltage level proportional to distance of travel of the scanner head 10. This DC voltage is converted to a digital binary word by the position A/D converter 81 shown in FIG. 8 and FIG. 9b.

After sufficient time has elapsed (about 200 μs for 100 mm of range) for the range counter or counters 82 to contain an appropriate count, the position of the scanner head is determined by the processor. Immediately following this, the data in the range counter 82 is read. The range count which resides as the number of counts per unit of system clock time is used to calculate the "range" or distance from the transducer face to the tissue interface responsible for generating the echo. For the case when the firing transducer and the transducer receiving the echo are the same, this is accomplished by the equation: Range = round trip distance/2, or Range = (velocity of sound in tissue) × (time to receive echo/2). Using a range counter clock frequency of 1.23 MHz and an average velocity of sound in tissue of 1540 m/s, this equation reduces to Range = 0.63 × COUNT, where COUNT is the number of the range counter. Corrections to this range are preferrably made for listening transducers which are not the same as the firing transducers using fundamental trigonmetric relationships.

In the discussion below the notation Y(J)·X(I) shall designate a memory matrix allocated to store "raw" range data. Raw is taken to mean unsmoothed or otherwise uprocessed data. As an example, a range calculation of 30 mm derived from the echoes detected by $T_0$ transducer at the uppermost position of the scanner head would be entered in the raw data memory matrix as Y(0)·X(0)=30.

The process described above is repeated under microprocessor control until the scanner head 10 has descended through all the "J" increments of interest. The raw range data matrix is therefore filled from the first Y(0)·X(0) element to the last Y(479)·X(15) element following the example set forth. It should be appreciated that the entire process of sound transmission, reception or retransmission, echo discrimination, and data storage occurs very rapidly relative to the rate of movement of the scanner head 10. Thus, the scanner head does not have to start and stop, but rather moves continuously down the back once the scan is initiated. The processing of this stored data is described later.

As alternative embodiment of the invention includes two range counters 82. In this embodiment a detection algorithm may be mechanized in which two range values may be ascribed to the first two echoes to exceed prescribed thresholds. Such an algorithm is useful as a bone edge detector.

As described, range counter No. 1 (FIG. 9e) begins counting when a sound wave is launched from a transducer element. The counter is stopped by a signal at input YY. The final count in range counter No. 1 is indicative of the range or distance from the transducer to the first tissue structure of interest nearest the transducer. After the microprocessor 75 reads range counter No. 1, the microprocessor resets this counter by appropriate signals on J1-20 (reset line) and J1-24 (strobe line).

The second range counting system (FIG. 9f) and specifically counter 82I also begins counting when a sound wave is launched from a transducer element. If a second more distant tissue structure of interest is detected, counter 82I is stopped by the presence of a stop signal on YY of FIG. 9f. Counter 82I will not be stopped by the first detected echo, because line XX will not go high (logical "1") to enable a stop signal to be recognized by 82I until a first echo occurs. The contents of 82I thus represent the range to the second tissue interface of interest, and it may be read by microprocessor 75. Subsequently, range counter No. 2 is reset after being read via lines J1-20 and J1-24. In the event a second echo is not detected, counter 82I will overflow and thus automatically reset.

Another alternative embodiment includes linear position transducer 20 (FIG. 5b) which provides the position of each transducer, such as 28, along the "Z" direction, that is a direction perpendicular to the field or plane of scan defined by the "X" and "Y" coordinates referred to above. This position is fed into the microprocessor (or control console 27) to refine the range values or in order to determine the range values with respect to an absolute plane, rather than in respect to the relative plane of the back. Such absolute range values may be useful in the diagnosis of certain aspects of scoliosis.

Shown in FIG. 8 is a high-speed A/D converter and memory buffer system 85 which is connected by dashed lines to the main scanner system. This part of the system is primarily for research purposes and may be brought "on line" as an option. The circuitry for this part of the system is shown in FIGS. 9g.1, 9g.2, 9h.1, and 9h.2 and the characteristics are described below. Since echo patterns are extremely transient in nature, the high-speed A/D converter and memory buffer 85 provide an ultra high-speed means of examining a designated echo pattern. When in use the memory buffer is always saving a prescribed number of scan lines or J lines of continuous echo amplitude data. For example, if the standard echo detection algorithm provides questionable data in some portion of the field scan, the appropriate contents of the memory buffer system may be interrogated under software control to recreate the analog echo pattern in this specific region of interest. The validity of the echo detection algorithm in this region of question may then be examined.

A smooth planar surface tends to reflect a sound beam according to Snell's law (i.e., angle of incidence equals angle of reflection). Thus, in such a simple case, the maximum "signal strength" of the echo pattern is obtained when the incident beam is perpendicular to the reflecting interface. In most practical cases, and in particular, with the irregular surface geometry of the bony structure of the ribs and spine, this ideal condition does not exist for all components of the target. An incident sound beam, although it can be focused, cannot be made infinitely narrow and, therefore, at least some minimal energy will return to the transmitting transducer unless the target surface has an extremely oblique angle relative to the face of the transducer. To enhance the probability of receiving echoes from bone returning not along the longitudinal axis of the sending transducer, the Multireceiver mode of operation was devised. In its simplest version, the Multireceiver algorithm is designed to operate in conjunction with a single row of transducers as shown in FIGS. 3 and 5a. A more sophisticated but more effective technique employs several rows of transducers as illustrated in FIGS. 6 and 7.

In the basic Multireceiver algorithm, a transducer (e.g., $T_2$ of FIG. 5a) launches a sound wave and then the same transducer $T_2$ listens for echoes. If no echoes are received, $T_2$ refires, only adjacent transducer $T_1$ now listens. If still no echo, $T_2$ refires and the other adjacent transducer $T_3$ listens. Following this procedure, the next transducer in normal sequence (namely $T_3$) fires and listens. If no echo, $T_3$ refires; $T_2$ listens. If no echo, $T_3$ refires, $T_4$ listens and so on. Because the adjacent transducer elements are intentionally located close together, very little error in calculated range values occur whether the launching transducer receives an echo or an adjacent transducer receives an echo. Nevertheless, errors in range values may be minimized by making fundamental trigonometric calculations which compensate for the displacement between transmitting and receiving transducers.

The Multireceiver algorithm may be extended to operate in conjunction with a multirow set of transducer elements as partially indicated in FIG. 6. Only twelve elements are shown in the figure, but compatibility with the forgoing example would indicate use of (16×3) or 48 transducer elements arranged as suggested in FIG. 6. In this embodiment, the trio of elements $T_1$, $T_{17}$, and $T_{33}$ are mounted in a common shoe affixed to a plunger. Note the slant in the orientation of the elements as opposed to vertical orientation. This feature allows minimization of the spacing in adjacent transducers. If transducers $T_0$, $T_1$ and $T_2$ were fired in sequence, there would be significant physical separation; however, if $T_{17}$, $T_1$ and $T_{33}$ are activated in sequence with proper adjustment in the J level corresponding to the Y dimension on the back, the physical separation between transducers in the X direction is reduced to zero (or, in fact, could produce overlapping beam widths).

In an extended version of Multireceiver (referring to FIG. 6), $T_1$ fires and listens. If no echo $T_1$ fires again, $T_0$ listens. If no echo, $T_1$ fires and $T_2$ listens. If no echo, $T_1$ continues to fire and in sequence $T_{17}$, $T_{18}$, $T_{32}$ and $T_{33}$ would listen. That is to say, those transducers "surrounding" the designated firing transducer are given the opportunity to capture a valid echo.

At any stage in the sequence, a valid echo terminates the iteration of listening transducers and transmitter control is passed to the next adjacent transducer, namely $T_2$. The sequence is then repeated in similar fashion. Consequently, the ability of the Multireceiver algorithm to capture off axis echoes is effectively extended from one dimension (X) to two dimensions (X and Y). That is, if required, the four transducers surrounding each "center" transmitting transducer may be designated as listening transducers.

The main purpose of the echo processing electronic circuits which are under control of the microprocessor is to detect ultrasonic echoes and to calculate the distance from the transducer to the structure that reflected the ultrasonic pressure wave.

In general, echoes will occur whenever the transmitted ultrasound encounters a bone and muscle (or soft tissue) interface, a muscle and lung interface, or even a skin and muscle interface. The size of the echo depends on several factors; the characteristics of sound (velocity and attenuation) in each medium and the angle of incidence of the sound and the interface.

The scanner head electronics is shown within the dashed lines of FIG. 8. The sixteen transducers (shown in FIGS. 2, 4 and 5a) are mounted side-by-side, making up a horizontal array approximately six inches wide.

Each transducer has a separate drive circuit 71D (FIG. 9c) which can be addressed by the microprocessor in various patterns; the usual pattern is to begin at the left and sequentially activate each transducer. The drive circuits supply a short, high voltage (200 to 500 volts) pulse to the transducers. This causes an ultrasonic pressure wave to travel out from the surface of the transducer. This pressure wave travels through body tissue at a typical velocity of 1540 m/sec and the tissue attenuates it by an average of 2 db/cm.

Echoes produced by bone/tissue interfaces return to the transducer surface and cause an electrical response in proportion to the magnitude of the echo as has been previously explained.

Immediately after the transducer is activated, the designated listening transducer is connected to a receiver and amplifier circuit (FIG. 9c), such that any returning echoes can be amplified and processed further.

The linear preamplifier 74 located on the scanner head 10 provides only a small amount of gain, but does provide the necessary drive to send the signal back to the main electronics package 60.

In the circuit of FIG. 9d.1 the nonlinear time dependent gain amplifier 76 includes a dual gate field effect transistor (FET) 76B. One gate, 76E of the FET controls the gain characteristics and the other gate 76F is the echo signal input. The SIGNAL AMP (back panel adjustment) control 76G is connected to the echo signal input gate 76F. By keeping the control gate 76E at a negative potential, the signal on the other gate does not appear at the output of the FET. As the voltage level on the control gate 76E increases, the gain of the FET increases until the maximum gain is reached. By changing the voltage level on the control gate 76E of the FET it is possible to have a time of zero gain and a time when the gain is increasing linearly towards the maximum gain. Ideally, the gain would never be less than one, however, because of transducer ringing it is necessary to have zero gain for several microseconds following the activation of the transducer. By controlling the time until maximum gain is reached corresponding to a depth of one to five centimeters the attenuation of the signal by tissue can be compensated.

Of the seven external back panel adjustments, four are related to the control gate signal. These four are RAMP OFFSET 76H, DELAY 76I, SEGMENT 1 76J, and SEGMENT 2 76K. These potentiometers are located in the circuit of FIG. 12d. The RAMP OFFSET 76H adjusts the negative potential on the control gate 76E. The DELAY 76I adjusts the time at which the amplifying process begins relative to the launching time of a sound wave (time zero). The profile of the time-gain characteristic may be regarded as having three segments. The slopes of the first and second segments are determined by the settings on the SEGMENT 1 76J and SEGMENT 2 76K controls respectively. The gain of third segment is inherently the maximum gain available from the amplifier. The WINDOW (bank panel adjustment) control 76L sets the maximum allowable time for amplification.

The time-gain amplifier described above plays an important role in distinguishing echoes from the ribs and spinal column from other echoes, in one aspect of the invention. A time-gain amplifier is an amplifier in which the gain can be changed over a specified time period. An ultrasound signal traveling through tissue suffers approximately 2 db/cm attenuation, thus the amplifier may be adjusted to compensate for the attenuation by increasing its gain at a rate of 2 db/13 $\mu$s (the speed of sound in tissue results in a round trip time of 13 $\mu$s, i.e. to travel 1 cm and back).

However, for the purpose of detecting echoes from ribs and vertebra, the optimal amplifier gain versus time curve is not simply one of increasing gain at a 2 db/13 $\mu$s rate. The following specific characteristics make the amplifier time-gain characteristics closer to the ideal for detecting echoes from ribs and the spinal column: (1) There is an adjustable time of zero gain (delay adjustment 76I) which corresponds to a depth of from 0 to 1 cm of tissue. This allows adjustment of the instrument to eliminate ringing artifact from the transducer pulse and also any false signals that might be generated at the transducer/skin interface; (2) there are controls for modifying the shape of the time versus gain curve during the time from 13 μs to 130 μs which corresponds to a tissue depth of from 1 cm to 10 cm. These controls enable a piecewise logarithmic gain characteristic to be constructed over various portions of the 13 to 130 μs time span. In the present implementation two such controls are provided; they are Segment 1 (76J) and Segment 2 (76K). Clearly any number of such controls as may be found necessary to construct an appropriate gain characteristic in other embodiments may be used.

As described below, in an optional embodiment the invention using a high-speed analog-to-digital converter, the gain changes are done in a closed loop fashion under the control of the microprocessor. The microprocessor increases the gain in an area where it expects echoes and decreases the gain where none are expected. The areas where echoes are expected (i.e. have a higher probability of occurring), may be "learned" by the computer from one or several previous scans at a slightly different anatomical position or by repeated scans in the same location with different gain versus time profiles. In other words, in this embodiment the ultrasound time-gain amplifier is "trained" for optimal amplification.

The RF detector (FIG. 9d.2) full wave rectifies the echo and applies this rectified signal to the comparator also shown in FIG. 9d.2. The comparator has an adjustable threshold setting 83D called DETECTOR THRESHOLD (back panel adjustment). Thus, only echoes above the threshold are detected.

When an echo is detected, the range counter of FIG. 9e is stopped. The count that has accumulated (corrected in some cases by trigonometry) corresponds to the range (or depth) of the structure that produced the echo. The resolution of the range counter in the preferred embodiment is 0.6 mm.

A second counter which is indicated in FIG. 9f can also be started when a transducer is fired. This gives the capability of calculating the range for the first two echoes that exceed the comparator threshold, or otherwise satisfy a prescribed detection criteria.

Not every transmission produces an echo. There are many possible reasons for not getting an echo large enough to trigger the comparator. The target may have been at such an angle to the incident sound wave that the echo may not return directly to the detector, or there may not have been a target within the maximum range of 15 cm. The application of the Multireceiver mode in alleviating these problems has been discussed.

In order to examine the analog echo signal in the event that echoes are not detected, a high-speed analog-to-digital (A/D) converter (FIGS. 9g.1, 9g.2, 9h.1 and 9h.2) can be brought on line under software control. The A/D converter 85B employed is a TRW model TDC1007PCR module. The 8-bit A/D converter output goes to an array of shift registers, such as 85C, that can hold 1024 8-bit conversions of the analog echo signal. The conversions are made at a 10 MHz rate; therefore, 102.4 microseconds of data can be held in the shift registers. The data can then be automatically clocked out of the shift registers at a slower rate providing a data expansion capability.

Alternatively, the data in the shift registers can be stored in the microprocessor memory 75A and 75B. Each 100 microseconds of data would require 1K of memory.

Examination of this data allows a more desirable detector level setting or gives insight into a more intelligent nonlinear gain curve characteristic. To enhance the probability of detecting echoes the detector level may be adjusted dynamically. For example, if an echo is not detected after a transmission, the detector level may be decreased and a second transmission made. If an echo is still not detected, the iterative process of detector level shifting and retransmission could be continued.

The position A/D converter 81 (FIG. 9b) provides a signal proportional to the vertical position of the scanning array. When the appropriate vertical distance (Y direction) has been scanned, the microprocessor 75 will stop activating the transducers 70 and inform the operator that the scan is complete.

The range data from each of the echoes received during a scan are stored in the microprocessor's memory 75A and 75B. This information is available for future processing and is used to generate a display that shows the spine and ribs.

DATA ACQUISITION AND PROCESSING

Figure 10:
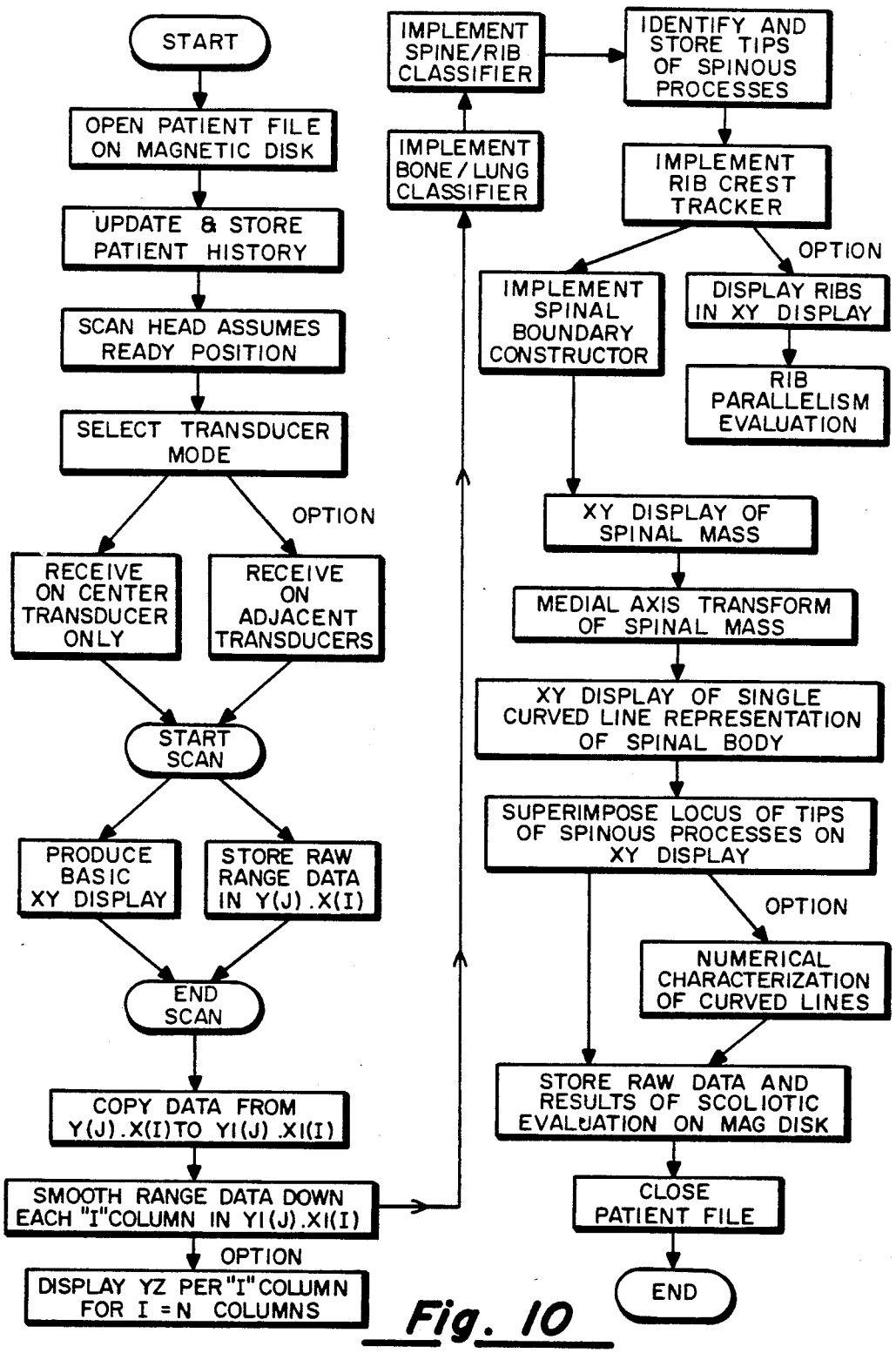
FIG. 10 shows a flow diagram for the preferred embodiment of the method according to the invention indicating the progression of scanner startup, data acquisition and data processing.

FIG. 10 is a flow diagram indicating the progression of scanner startup, data acquisition, and data processing. Certain optional decisions selected via the keyboard 80 are indicated which, in general, yield intermediate displays and supplemental results on route to the final characterization of the curvature of the patient's spine.

After the instrument is powered up, the patient's name and/or a file number is entered. For a returning patient, a summary of the results of the previous evaluation is read from floppy disc memory 75D and presented on the CRT 65 of the console 60. For a new patient, a new file on magnetic disc 75D is created and the relevant aspects of the patient's history are entered. When the patient is prepared for the scan, a command at the keyboard 80 causes the scanner head 10 to automatically seek the "ready" position along the transport rails 33A and 33B. Subsequently, the mode in which the transducers 12 are to operate is selected. The scanner head 10 is then pressed against the patient's back such that the individual transducer elements 12 are in positive compression against the patient's skin 11. The transport system's reference points, cervical 31 and sacral 32, are correctly aligned on the patient's back 11 by palpation.

A keyboard command, or alternatively, momentary depression of a remote start button 64 (FIG. 1) mounted on the transport system 30 initiates the scanning procedure. As the scan is progressing under software control, a real time display is presented on the CRT 65 of the system console 60. This shall be known as the Basic XY display. A portion of the 512×512 dot matrix CRT field is selected to be a proportioned scale replica of the XY field of scan on the back 11 of the patient. Therefore, in the example set forth using sixteen transducer elements, a field of 16 pixels by 480 pixels represents the back 11 of the patient. At the beginning of the scan this CRT field is darkened. The Y(J)·X(I) memory matrix which is used to drive the CRT pixel field is initialized with all elements set to range values of 150 mm. A range value of 150 mm is arbitrarily chosen as the maximum range value of any relevance for our purposes. Therefore, the "background" value for this imaging becomes 150 mm. As the scan proceeds, each calculated range value is tested against a criteria of being between (but not equal to) 0 mm and 150 mm. If this condition is met, the memory value of 150 is replaced with the new range value and the corresponding pixel on the screen is lighted.

It is important to note that the rate of travel of the scanner head 10 down the back 11 of the patient is very slow compared to the rate of firing of the transducers 12. A typical scan requires a half minute to a minute to complete, whereas the firing and listening sequence of 16 transducers at a particular J level may be completed in 100 ms. It was determined experimentally that it was desirable to have each transducer 12 interrogate the same elemental region of the field of scan more than once so as to enhance the probability that relevant echoes would be received. Therefore, the system is adaptable so that there are multiple opportunities for acquisition of echo data and hence the replacement of the initialized range values (150 mm). A software option is discussed below for averaging of multiple attempts or the presentation and display of the contribution to end results from multiple attempts. Once the background value of 150 mm is replaced, it was found desirable to "lock-out" further attempts to change the range value during the same scan.

The echo signal amplifiers 74 and 76 and detection system 83 were designed and adjusted so that there is a high probability of triggering the discriminator 83 and hence producing a valid range value at each discrete element in the field of scan even though the transmitted sound wave does not encounter bone. This occurs because a large portion of the scan field is in the thoracic region. In this region the lungs and plural sac of the lungs are in close proximity to the ribs. In viewing the patient from the back, the ventral aspect of the ribs is in apposition with the plural sac. Experimentally, it was found that significantly strong echoes are returned from this plural tissue interface between the ribs. Importantly, the average range values returned in the intercostal spaces are larger than those range values returned from dorsal aspect of the ribs. The average difference is the thickness of a rib (5 mm to 10 mm) and this formulated the basis of the software which extracts rib from lung, i.e., the Bone/Lung Classifier.

Upon completion of the scanning operation, the Y(J)·X(I) data matrix is filled with raw data. This data is then copied into the $Y_1(J) \cdot X_1(I)$ data matrix. The data in the $Y_1(J) \cdot X_1(I)$ matrix is processed and changed while the Y(J)·X(I) matrix preserves the raw data which is eventually transferred to magnetic disc storage 75D under the patient's raw data file. Next, the $Y_1(J) \cdot X_1(I)$ data is subjected to a routine smoothing operation. The data is smoothed down each "I" column. This data may then be displayed as illustrated in FIG. 11.

Figure 11:
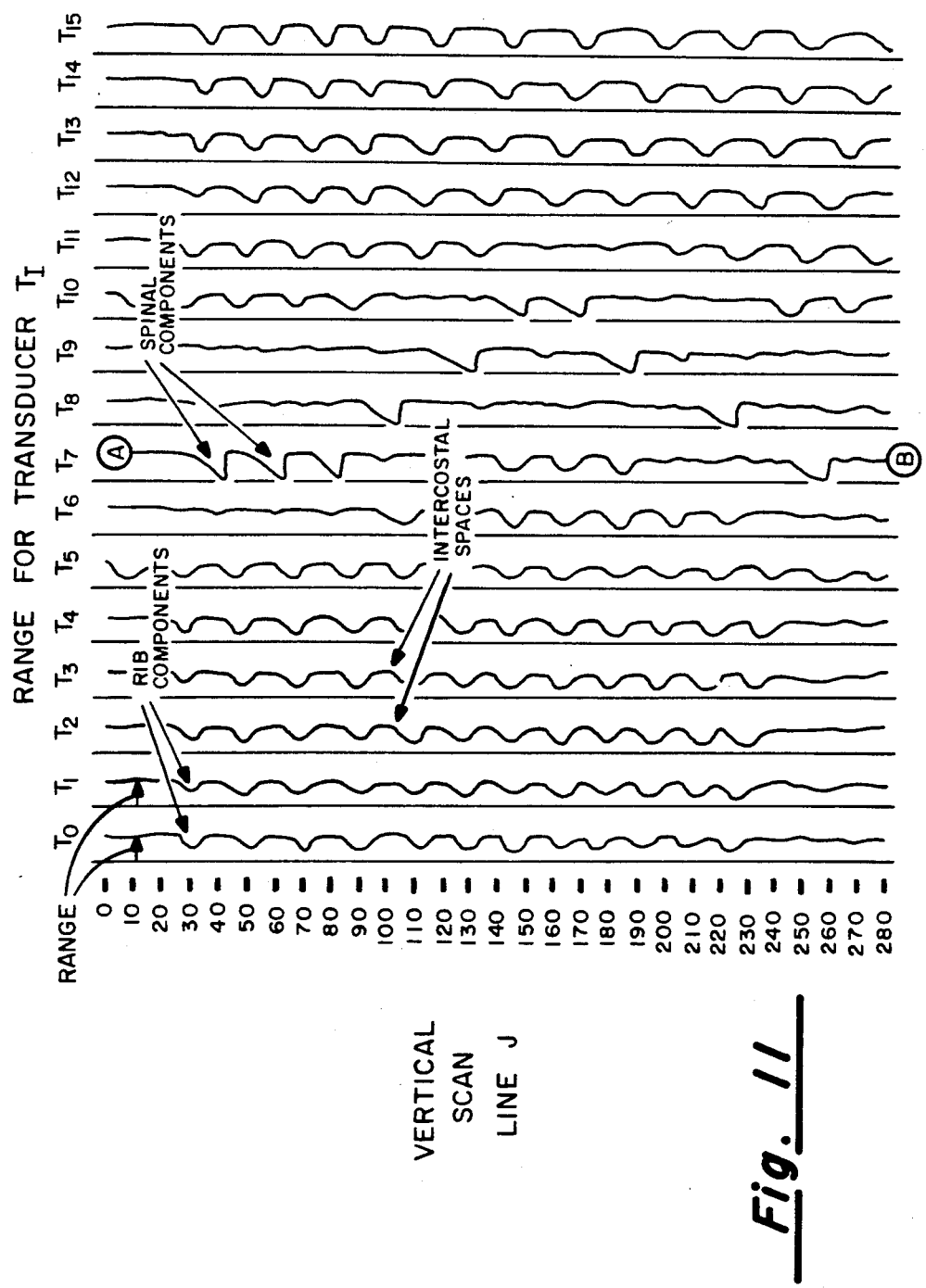
FIG. 11 shows an exemplary profile plotting range versus transducer position for an embodiment of the invention utilizing sixteen transducers.

FIG. 11 may be considered a composite display of the results obtained from each of the "N" individual transducers 70 (sixteen in the exemplary embodiment). Each column $T_0$ through $T_{N-1}$ shows a range profile or range "signature" for each transducer 12 as it traversed the back 11 from $J_{begin}$ to $J_{end}$. In each column of FIG. 11 the line to the left of each signature is the zero range reference line which is the face of the transducer 12. The primary concept to be conveyed by FIG. 11 is that as the transducers move down the back, range signatures are generated which have geometric attributes germain to the anatomy of the skeleton underlying the transducers. For example, in FIG. 11, the ribs appear as "humps" with rounded or flattened tops. Intercostal spaces are relatively straight lines connecting the rib humps. More triangular or jagged peaks are characteristic of spinal components—primarily spinous processes and certain aspects of the transverse processes. Interestingly, it was determined that there is a high probability that the nonsporadic absence of echoes in a region is the result of incident sound waves striking spinal components. The manifestation of this would be breaks in the range signatures of FIG. 11. This phenomenon is due to the complex geometry of the spinal components and in particular the obliqueness of the surfaces of the spinal components relative to the face of the receiving transducers. In these situations, the probability of echoes returning directly to the transmitting transducers is lowered. Nevertheless, identification of this phenomenon and application of the Multireciever mode is useful in the data acquisition and subsequent classification of skeletal components.

Using this information, then, it is possible to implement the Bone/Lung Classifier indicated in FIG. 10. In conjunction with this data processing, the Spine/Rib Classifier is implemented. The predominate feature of this algorithm is the extraction of those range values associated with the peaks or crests of the rib humps and spinous processes from the range signatures of FIG. 11. A display of the results in the same format as in FIG. 11 yields the display illustrated by FIG. 12. Any identification of the tips of the spinous processes (illustrated as squares) results in the memory storage of the associated range values and the (J, I) coordinates for later use in the assessment of vertebral rotation.

Figure 12:
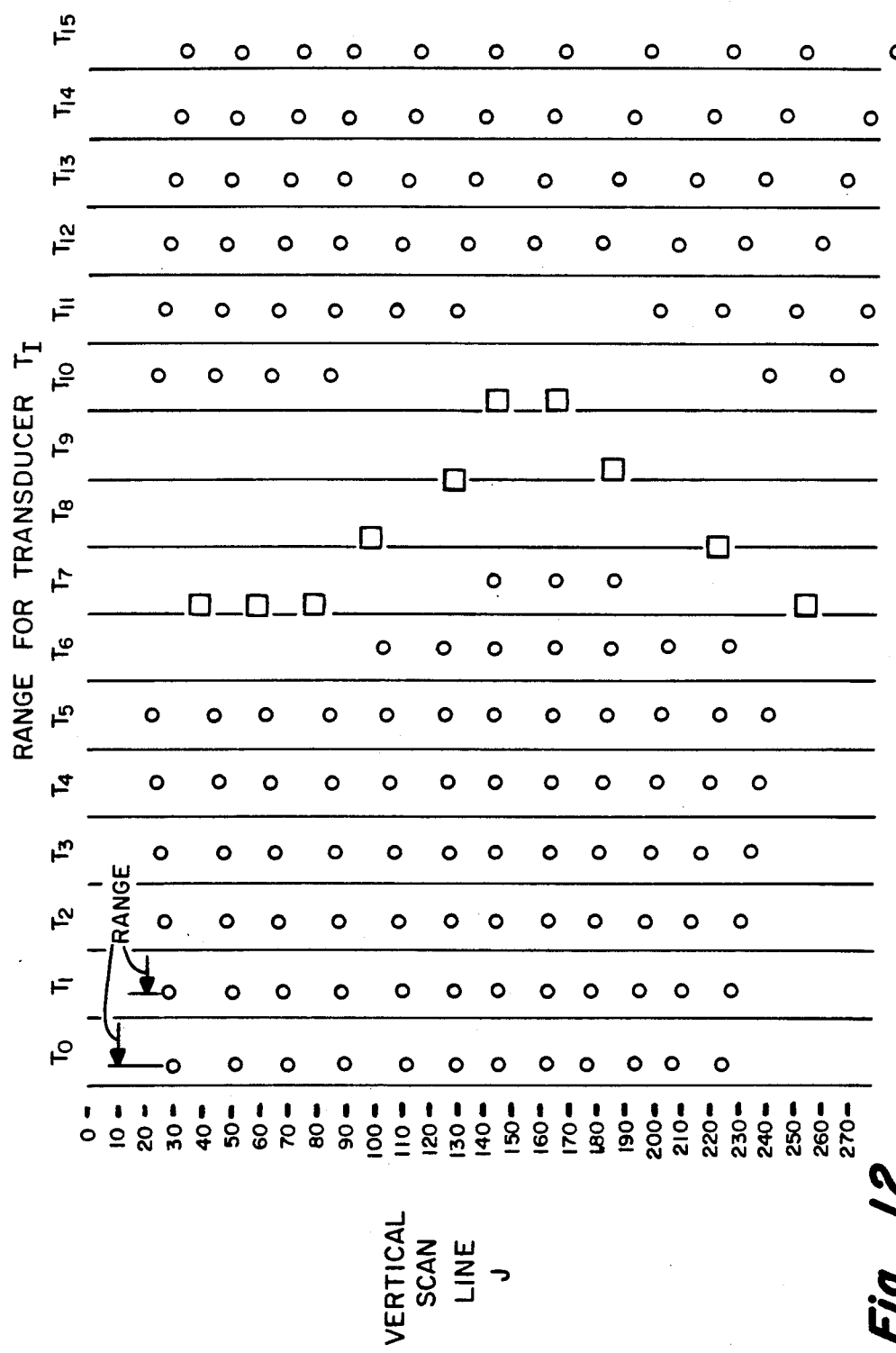
FIG. 12 shows an alternative embodiment of the profile of FIG. 11 in which the position of the ribs have been identified by circles and the position of the spinous processes have been identified by squares.

Next, the data points indicated in FIG. 12 are processed such that the rib crests (illustrated as circles) are effectively connected. The algorithm for this is referred to as the Rib Crest Tracker in FIG. 10. These results may be optionally displayed in the format of the Basic XY display which is illustrated in FIG. 13. As previously stated, this display is scaled in the X and Y directions proportional to the X and Y dimensions of the patient's back. Hence, this display indicates the relative position of ribs as projected on the XY plane. The relative "angles" of the ribs and their relative parallelism is indicative of spinal curvature. Note, for example in FIG. 13 the locus of points which are connected on the left converge to the left and the locus of points which are connected on the right diverge to the right. This nonsymmetry is indicative of a clinical situation of abnormal lateral spinal curvature coupled with rotation of the vertebrae. On the concave side of a curve in the spine, the ribs tend to converge or close together whereas on the convex side of the curve the ribs diverge or become more widely separated.

A Spinal Boundary Constructor algorithm is next implemented. The result of lighting all pixels representing the boundary of ribs and spine on the left and right side of the spine produces the display shown in FIG. 14. The next step involves implementing an algorithm which is referred to as a Medial Axis Transform of the spinal mass. The objective of the Medial Axis Transform is to find the "best" center line or medial axis through the two-dimensional irregular spinal mass shown in FIG. 14. The result of performing this operation is the solid line 94 in the display of FIG. 15. The solid line 94 thus becomes a single line representation of the lateral curvature of the spine. The X and Y coordinates of this line are stored in memory and may be used to mathematically characterize the curved spine as any curved line may be characterized. Also, the results may be output in the form of hard copy graphics on the CRT 65 or printer 84C. By making a transparency of the hard copy, the results of subsequent evaluation may be compared by overlaying the transparencies.

Figure 15:
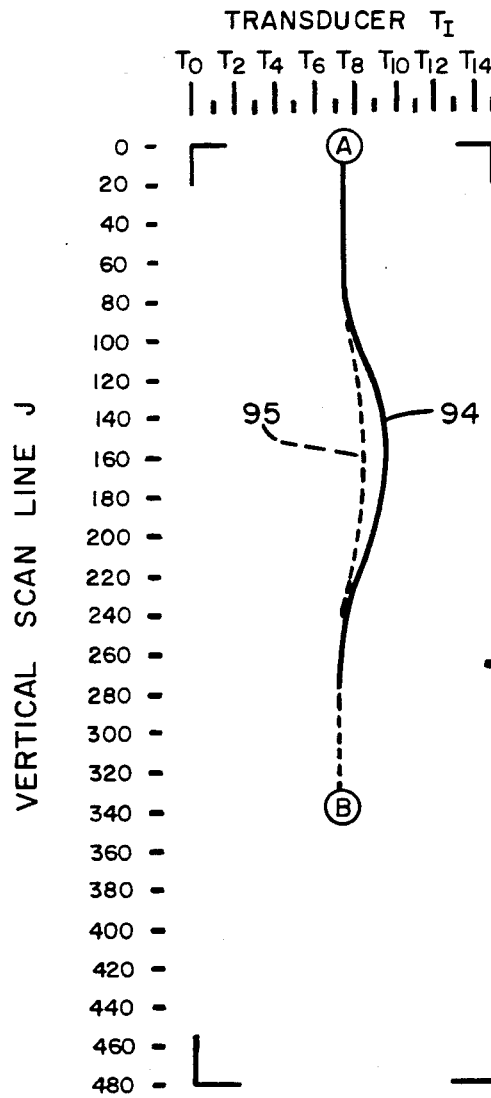
FIG. 15 shows the results of performing a medial axis transformation on the data of FIG. 14 in order to characterize the spinal curvature and spinal rotation associated with the data of FIG. 14.

The broken line 95 indicated in FIG. 15 is a display of results related to vertebral rotation. Most often in the clinical examination of scoliosis it is found that the vertebrae tend to rotate with spinous processes and pedicles deviated toward the concave side of the curve. The broken line 95 of FIG. 15 is thus a display in the XY plane of the locus of the tips of the spinous processes which is derived from the displayed data (squares) of FIG. 12. In a normally "straight" spine the solid and broken lines 94 and 95 of FIG. 15 would be essentially coincident. Consequently, a measure of the noncoincidence of the two lines of FIG. 15 is, in essence, a measure of the degree of rotation of the spine associated with the scoliosis.

The data processing is concluded as indicated in FIG. 10 by the storage of the results of the scoliotic examination on the patient's permanent file residing on magnetic disc 75D. The file is then closed. The system may then be initialized for the next examination.

SOFTWARE

The software which was developed for the scanning system was written exclusively in the Intel PLM-80 language. Listings of all the relevant programs developed and debugged appear in the Appendix. A knowledge of PLM-80 coupled with numerous program comments in the listings allow the reader to follow the programs quite readily. To further aid this process and to enhance the appreciation of how the various algorithms were mechanized, a brief discussion of the software follows.

In the discussion which follows there will be reference to the names of programs and to the names of procedures. A modular approach to software management was employed. This means that a number of programs were written which, in turn, contain numerous procedures or subroutines. This is to be contrasted with one huge program. Modular programming facilitates changes and additions because only the particular program containing changes need be compiled following the changes. All programs are effectively joined into one large program by the process of "linking" which is done automatically on command to the microprocessor development system.

SCAN21.PLM is the Scanner's main program, or MAIN$-MODULE. Main in the sense that this program initializes a number of variables and prepares the system for use when the power is turned on. SCAN21 perpetually interrogates the Scanner keyboard 80 to see if any commands have been entered. When selected keys are pressed, SCAN21 makes the appropriate calls (or jumps) to other routines in the system. The listing of SCAN21.PLM (see Appendix) includes as comments a menu of choices for keys. For example, to initiate a new scan, either keys 1 (calls BASIC$SCAN-$PROCEDURE), 8 (calls MULTI$RECEIVER$PROCEDURE), or 9 (calls MULTI$CENTER$FIRE$-PROCEDURE) would be pressed.

SCAN21.PLM also contains procedures for copying or transferring the contents between the various data matrices which are established, namely Y(J)-X(I),Y$_1$-(I)-X$_1$(I) and Y$_2$(J)-X$_2$(I).

The SCAN10.PLM file is referred to as the FUNDAMENTAL$XY$SCAN$MODULE. This module contains the procedures XY$REG, DISPLAY$1, DISPLAY$1A, BASIC$SCAN, and RESCAN.

BASIC$SCAN provides the software for positioning the scanner head 10 at the ready position. Then all range values in the Y(J)-X(I) and Y$_2$(J)-X$_2$(I) matrices are preset to 150. BASIC$SCAN starts the descent of scanner head 10 and a loop sequentially transfers control from transducer to transducer across the array. At each transducer, such as 12, flags are examined to determine the receiving mode and flags are set to later be examined by an XY display routine to determine which pixels in the scan field should be lighted.

DISPLAY$1 and XY$REG work together to locate the pixel in the XY field to be lighted or not lighted as determined by information in the data matrices. DISPLAY$1A may be called from other programs to turn off previously lighted pixels.

RESCAN simply reconstructs the Basic XY display based upon the most recent scan whenever it is called. The original XY display is constructed in real time as the scan head moves. RESCAN is used to recall the XY display after it is erased from CRT 65.

SCAN12.PLM is the MULTI$RECEIVER$-SCAN$MODULE and it contains the procedures MULTI$RECEIVER and MULTI$CENTER$FIRE. MULTI$RECEIVER contains the software needed to control the transducers, such as 12 in a fashion such that reception of incoming echoes may occur on either the right or left transducer adjacent to the designated transmitting transducer. The structure of the MULTI$-RECEIVER algorithm truncates the iterative process of transmitting with a designated transducer and listening with adjacent transducers as soon as a valid echo (range value less than 150) is detected. Additionally, echoes detected by the "center" or designated transmitting transducer may be separated from those subsequently detected by the "adjacent" transducers.

MULTI$CENTER$FIRE is a routine which will fire the "center" transducer for a preselected variable number of attempts at a particular J value (Y coordinate) in the field of scan in an effort to obtain an acceptable echo before it stops trying and passes control back to the calling program.

Referred to as the ACTIVATE$TRANS-DUCERS$MODULE the F5.PLM program contains the procedures FIRE$RECEIVE$SELECT, FIRE$-CENTER$RECEIVES$CENTER, FIRE$CENTER$RECEIVE$RIGHT, and FIRE$CENTER$-RECEIVE$LEFT. FIRE$RECEIVE$SELECT controls the switching logic to implement a code which is sent to 1 to 16 selector 72 and received signal multiplexer 73 for designating an active (transmitting and/or receiving) transducer and then applies a trigger pulse to fire the selected transmitting transducer via transducer drive circuit 71D. The other procedures in this module perform functions exactly as their respective names imply.

The R4.PLM program is referred to as the DETERMINE$RANGE$MODULE. Whenever the procedure DETERMINE$RANGE is called, the count in the range counter 82 is read and a calculation is made to determine the corresponding distance in millimeters to a target component. Presently, this calculation is based upon an average velocity of sound in tissue of 1540 m/s.

CTR70.PLM is the YZ$BY$COLUMN$DIS-PLAY$MODULE and contained within it are the procedures BOUNDARY$LINES, COLUMN$MIN$-MAC$SEARCH, YZ$DISPLAY, YZ$DISPLAY$-LEFT, YZ$DISPLAY$CENTER, YZ$DISPLAY$-RIGHT, and YZ$DISPLAY$TWO. In general, the purpose of this module is to generate a display on the CRT 65 which a composite plot of Z (range) values versus Y position for each transducer element (T$_j$ column). BOUNDARY$LINES divides the face of the CRT 65 into columns separated by dashed vertical lines which are equidistant apart. Each boundary line gives a zero reference for the corresponding position of the face of transducer 12 in the Z dimension. YZ$DISPLAY keeps track of the column into which a particular range value should be plotted and examines flags which indicate whether results from "single receiver", "multireceiver", or a composite of the two should be presented. The rest of the procedures select and display either a left, right, or center section of the transducer columns. YZ$DISPLAY$TWO compresses the results of left, center and right into one picture, but boundary lines between columns are dissolved.

CRT70.PLM also contains a procedure called COLUMN$MIN$MAX$SEARCH. This routine implements a search through the raw data matrix I column by I column. The output of this routine is the construction of three one-dimensional arrays which contain the minimum valve, maximum value, and difference between min and max for each I column.

Known as the ISOMETRIC$DISPLAY$MODULE the CRT51.PLM file contains subroutines which produce an isometric three-dimensional box or frame around the plotted data. The subroutine END$POINTS$1 locates each data point in the three-dimensional space. The procedure requires no trigonometric function calculations. Instead the program was written to employ 4, 12, 13 standard triangles. Positioning is then based on the concept of similar triangles, A procedure called CONNECT$POINTS1 serves to draw line segments between the data points. All line segments are drawn within a specified J value, i.e., for a given Y coordinate data point, a line segment is drawn to the next adjacent data point with the same Y coordinate. The program allows lines to be drawn only at specific intervals of J values. The method of geometry allows only three possible vector directions for line segment construction, namely zones of "vector 0" (0° to 90°), "vector 1" (180° to 270°), and "vector 2" (270° to 360°). The procedures ISOMETRIC$DISPLAY and ISOMETRIC$DISPLAY$TWO are similar in principle, but ISOMETRIC$DISPLAY$TWO plots data points (end points) for each value of J rather than intervals, of J, and further, the end points are not connected. Thus, the relationship of data points tends to be with respect to X value rather than Y values. In other words, ISOMETRIC$DISPLAY produces line segments for designated J values while ISOMETRIC$DISPLAY$TWO tends to produce line segments for designated I values.

The GRY3.PLM program is called the GRAY$SCALE$MODULE and it contains procedures referred to as MIN$MAX$SEARCH, GRAY$LEVEL$SET, and EIGHT$LEVEL$GRAY. GRY3.PLM develops an XY display of range values in an eight-level gray scale. The format is identical to the basic DISPLAY$1 routine except that the light intensity of each lighted pixel is indicative of the relative magnitude of the range value driving the respective pixel. The brightest pixels are the smallest range values. A call from MAIN$MODULE for EIGHT$LEVEL$GRAY initiates the process. The algorithm employs "auto-scaling." That is, the difference between the largest range value and the smallest range value is factored into establishing the scale as opposed to assigning absolute range values to particular light intensities. MIN$MAX$SEARCH locates the minimum value and the maximum value of all range values in the $Y_1(J) \cdot X_1(I)$ processed data matrix. Then the difference between the min and max is divided into eight bands. These partition ranges are referred to as slice 0 through slice 7.

GRAY$LEVEL$SET then evaluates each range value and assigns a gray level to it. The appropriate pixel in the XY field corresponding to the Z value or range value in question is located and turned off. Then it is turned back on at a light intensity proportional to its assigned level. The equation

MODIFIED$RANGE$PARTITION=(RANGE$SPREAD−(N$PARTITIONS*RANGE$PARTITION))/7 where
RANGE$SPREAD=MAX$VALUE−MIN$VALUE and

RANGE$PARTITION=RANGE$SPREAD/7 determines the width (range of values) contained within each level of gray. This equation was implemented because of the nonuniform distribution of range values. The majority of values cluster more toward the minimum rather than the center or the maximum values. Therefore, as the N$PARTITIONS factor (which was normally set at two) is increased, the width of each gray band shrinks thus yielding more resolution and the more the entire gray scale is shifted toward the minimum. As the RANGE$SPREAD is increased for a given N$PARTITIONS, each gray band widens.

A more elaborate, and perhaps better technique, would be to perform a statistical analysis of range data thus finding the mean and standard deviation. The gray scale could then be positioned optimally within this distribution. The gray scale image would, however, develop dramatically slower.

The CLASS1.PLM program is referred to as BONE$LUNG$CLASSIFIER$MODULE. The procedures within this module are JBAND$MIN$MAX$SEARCH, JGAP$TEST, INTP$RANGE, BONE$LUNG$ONE, INTERPOLATE, and BONE$LUNG$TWO.

BONE$LUNG$ONE and BONE$LUNG$TWO implement algorithms which have been discussed to some degree. The goal is to segregate range value attributable to bone from range values largely attributable to lungs or plural sac membrane. BONE$LUNG$ONE was developed first and operates in the following manner. Each I column in the $Y_1(J) \cdot X_1(I)$ processed data matrix is searched for a minimum and maximum value. Then a "decision line" is constructed somewhere between these limits. In the language of the program, the choice of a value for the variable DF determines where this decision line is drawn. Range values less than the decision value were classified as bone. If DF=4, for example, the decision line is drawn midway between the min and max. If $0 \leq DF < 4$, then the decision line was shifted toward smaller values of bone. Likewise, if $4 < DF \leq 8$, then the decision line is shifted toward larger range values. In general, a different decision value is selected for each I column in BONE$LUNG$ONE, but the decision is static for the column.

In BONE$LUNG$TWO, however, a decision value is dynamic in the sense that it is computed for each J value down the column. At each J value or "J Point" there is a look-ahead and a look-back for a total span of "J Band." The min and max values of range are found in the current J Band. Then the decision rule is applied as in BONE$LUNG$ONE. A value of 20 for J Band seemed optimal and this is primarily due to the fact that the rib spacing in the experimental data was about equivalent to twenty increments of J.

INTERPOLATE is called upon to fill small gaps in the range signatures down each I column. The routine is written such that when a gap in data is encountered, the width of the gap is tested (by call of JGAP$TEST) against a criteria which can be experimentally varied. For example, if the gap is no greater than five increments of J, then a call is placed to INTP$RANGE. INTP$RANGE then performs a linear interpolation to fill the gap with data.

SM1.PLM is the RANGE$DATA$SMOOTHING-$MODULE and it is implemented by a call from the main program to the procedure NONWEIGHTED$-SMOOTHING. The purpose of this routing is to smooth or average the range data down each I column thus producing a more attractive range signature containing less noise. For each J value in a column, $2K+1$ values of range are averaged, where K is the number of J values on each side of the center J Point. For this procedure, data is input from the $Y_1(J) \cdot X_1(I)$ matrix and "smoothed" data is output to the $Y_2(J) \cdot X_2(I)$ matrix.

RIB1.PLM is a program to evaluate a concept for identification and removal of rib data from the general data field. This program was only partially successful in that some of the non-spinal data which could be attributed to ribs was removed. Therefore, there are some attributes to the algorithm which could be included in an extensive rib removal algorithm. It should be noted that the illustrative program operates on data with fifteen columns, i.e., fifteen transducers are involved in data accumulating, rather than sixteen transducers as in other illustrations.

There are four subroutines in the present RIB1.PLM program. They are CENTER, RIB1$STRIP$ONE, RIB1$STRIP$LEFT, and RIB1$STRIP$RIGHT. A call from MAIN to RIB$STRIP$ONE initiates the process. RIB$STRIP$ONE sets values on several variables, and then in succession calls CENTER, RIB1$-STRIP$LEFT, and RIB1$STRIP$RIGHT. CENTER simply moves down (J=0 to 479) through the center of the raw data field (specifically columns $I_6$, $I_7$, $I_8$) and copies these range values to the processed data matrix $Y_1(J) \cdot X_1(I)$. RIB1$STRIP$LEFT and RIB1$STRIP$-RIGHT implement an algorithm which is based upon a rib model stating that range values for rib will increase as the transverse distance from either side of the spine increases. This is an oversimplified model, but it is at least partially true for regions along a rib.

RIB1$STRIP$LEFT works from the left toward the center of the data, whereas RIB1$STRIP$RIGHT works from the right toward the center. For a given row or J line, each range value in that row (i.e., $I_0$ through $I_5$ on the left, and $I_{14}$ through $I_9$ on the right) is compared to each value in an adjacent "element field." The dimensions of the field are set by the variables J$FIELD and I$FIELD. Best described by example, the algorithm was tested with a field of I$FIELD$-2$ (width) by J$FIELD $-5$ (length). The test value of $Y(5) \cdot X(0)$ would be compared with each value in the ten element field $Y(J) \cdot X(I)$ where I=1, 2 and J=0, 1, 2, 3, 4. If the test value was greater than or equal to any element in the field, then the test value was considered rib and was discarded. The test value would then become the next value over (increment I on left) in the particular J line and the elemental field would be shifted one column to the right (left for RIB1$STRIP$-RIGHT) but still maintaining the same field dimensions.

After completing the current J line, the identical process would be repeated for the next J line down.

It might be predicted that perhaps the only region of the rib where this algorithm would work well would be those portions under end transducers on the extreme right and left. In this region the ribs begin to curve anteriorly toward the thorax. There was significant removal of data immediately adjacent to the spine (e.g., transducers $T_4$, $T_5$ and $T_9$, $T_{10}$). One interesting possible explanation is that the boundary between rib and spine is partially being detected. Viewing a transverse section of the thorax in the vicinity of the junction of the transverse process to the rib known as the costotraverse articulation there is a "step." In viewing the left side of the spine, it may be found that the left side of this step is a rib. This is manifested as a greater range value when compared to the right side of the step which would be considered a spinal component.

The UPOS.PLM program contains the software to run an analog-to-digital converter connected to the scanner head transport system 30. A call to this program produces a digital number (J value) which defines the current position of the scanner head 10.

The CLEAR2.PLM files contains instructions required to erase the face of the CRT 65.

There has been described a novel system for ultrasound scanning which provides a method and apparatus for ultrasonic imaging when the target surface has an extremely oblique angle relative to the face of the transducer, such as when imaging portions of the skeleton, and is particularly suited for detecting the spinal curvature that is indicative of scoliosis. While the invention has been described in connection with a single preferred embodiment for the entire system and a number of alternative embodiments for particular parts of the system, one skilled in the art will appreciate that numerous other embodiments of the entire system and further alternative embodiments of various parts of the system and departures from the particular embodiments and alternative embodiments shown may be made without departing from the inventive concepts. For example, a wide variety of different scanner heads, scanner head transport systems, and computer control and processing systems and display systems and software may be used while still employing the inventive concepts. It is therefore to be understood that, within the scope of the appended claims, the invention may be practiced other than as has been specifically described.

What is claimed is:

1. An ultrasound imaging system comprising:
    a plurality of ultrasound transducers for generating an ultrasound signal, for receiving an ultrasound signal, and for producing a transducer signal representative of said received signal;
    means for providing a range signal representative of the distance of object interacting with each ultrasound signal;
    timing means for producing a timing signal;
    means for energizing said transducers;
    means for listening for an ultrasonic wave being received at one of said transducers and for producing a stop signal indicative of each ultrasound wave being received;
    sequencing means responsive to said timing signal and electrically connected to said means for energizing and said means for listening for selecting a sequence of firing transducers, for causing said means for energizing to fire a selected firing transducer at first determined time, for selecting a sequence of listening transducers and for causing said means for listening to listen to the listening transducers of the sequence during second determined times, said sequencing means also responsive to said stop signal for selecting the next in the sequence of firing transducers whenever said stop signal is received until said firing and said listening sequences are completed; and means responsive to said transducer signals and said range signal for producing an output representative of said received ultrasound signals.

2. An ultrasound imaging system as in claim 1 wherein said plurality of transducers is a linear array of transducers and said sequence of listening transducers comprises said firing transducer and one transducer on either side of said firing transducer.

3. An ultrasound imaging system as in claim 1 wherein said plurality of transducers is an $N \times M$ two-dimensional array of transducers where N is the number of transducers in each row and M is the number of transducers in each column, and wherein the centers of the transducers in each row are offset from the centers of the transducers in adjacent rows so that lines drawn through the centers of transducers in any row intersect at an angle other than 90° with lines drawn through the centers of transducers in any column.

4. An ultrasound imaging system as in claim 3 wherein said array comprises an $N \times 3$ two-dimensional array, the firing transducer is selected from the middle of the three rows, and said sequence of listening transducers comprises said firing transducer and the transducers surrounding each firing transducer.

5. An ultrasound imaging system as in claim 3 wherein, with respect to a rectangular coordinate system in the plane of the array, the edges of each transducer overlap with the edges of neighboring transducers in at least one coordinate direction.

6. An ultrasound imaging system as in claim 3 wherein, with respect to a rectangular coordinate system in the plane of the array, the separation between the edges of neighboring transducers in at least one coordinate direction is zero.

7. An ultrasound imaging system as in claim 1 and further comprising:

means for supporting said transducers and for moving said transducers along a determined path; and means for providing a position signal representative of the position of said transducers with respect to at least one predetermined reference point.

8. An ultrasound imaging system as in claim 7 wherein said means for producing an output comprises a means responsive to said electrical signal, said range signal, and said position signal for identifying signals indicative of the skeletal structure and for producing an output representative of the skeletal structure.

* * * * *

UNITED STATES PATENT AND TRADEMARK OFFICE
CERTIFICATE OF CORRECTION

PATENT NO. : 4,489,729
DATED : 25 December 1984
INVENTOR(S) : Sorenson et al.

Page 1 of 2

It is certified that error appears in the above-identified patent and that said Letters Patent are hereby corrected as shown below:

Column 1,
    Line 63, "warrented" should be --warranted--;

Column 4,
    Line 8, "9i d.1" should be --9d.1--;
    Line 62, "is" should be --in--;

Column 5,
    Line 51, after "in" insert --a--;

Column 6,
    Line 21, after "shoes" insert --14--;
    Line 24, after "provide" insert --a--;

Column 8,
    Line 24, "electroniccs" should be --electronics--;

Column 17,
    Line 34, "As" should be --An--;
    Line 51, "821" should be --82I--;

UNITED STATES PATENT AND TRADEMARK OFFICE
CERTIFICATE OF CORRECTION

PATENT NO. : 4,489,729
DATED : 25 December 1984
INVENTOR(S) : Sorenson et al.

It is certified that error appears in the above-identified patent and that said Letters Patent are hereby corrected as shown below:

Column 20,
 Line 30, "761" should be --76I--;
 Line 34, "761" should be --76I--;

Column 21,
 Line 53, "TDC1007PCR" should be --TDC1007PCB--;

Column 25,
 Line 57, "are" should be --were--;

Column 26,
 Line 43, the second "to" should be --of--;

Column 27,
 Line 17, "valve" should be --value--;

Column 29,
 Line 15, "routing" should be --routine--.

Signed and Sealed this

Fifteenth Day of October 1985

[SEAL]

Attest:

*Attesting Officer*

DONALD J. QUIGG

*Commissioner of Patents and Trademarks—Designate*